United States Patent [19]

Zakko

[11] Patent Number: 5,527,274

[45] Date of Patent: Jun. 18, 1996

[54] CATHETER FOR CHEMICAL CONTACT DISSOLUTION OF GALLSTONES

[75] Inventor: Salem F. Zakko, Farmington, Conn.

[73] Assignee: Development Collaborative Corporation, Hamden, Conn.

[21] Appl. No.: 998,424

[22] Filed: Dec. 30, 1992

Related U.S. Application Data

[63] Continuation of Ser. No. 482,194, Feb. 20, 1990, abandoned, which is a continuation-in-part of Ser. No. 180,099, Apr. 11, 1988, Pat. No. 4,902,276, which is a continuation-in-part of Ser. No. 871,775, Jun. 9, 1986, abandoned.

[51] Int. Cl.$^6$ .................................................. A61M 31/00
[52] U.S. Cl. .............................. 604/28; 604/35; 604/280
[58] Field of Search .......................... 604/27, 29, 30–31, 604/35, 43, 93, 95, 280, 281, 174–5

[56] References Cited

U.S. PATENT DOCUMENTS

| | | | |
|---|---|---|---|
| 3,119,392 | 1/1964 | Zeiss | 604/95 |
| 3,726,269 | 4/1973 | Webster | 604/281 |
| 3,902,492 | 9/1975 | Greenhalgh | 604/43 |
| 4,168,703 | 9/1979 | Kenigsberg | 604/280 |
| 4,245,624 | 1/1981 | Komiya | 604/95 |
| 4,329,994 | 5/1982 | Cooper | 604/98 |
| 4,573,966 | 3/1986 | Weikl | 604/101 |
| 4,583,968 | 4/1986 | Mahurkar | 604/280 |
| 4,655,744 | 4/1987 | Thistle | 604/28 |
| 4,733,652 | 3/1988 | Kantrowitz et al. | 604/96 |
| 4,777,951 | 10/1988 | Cribier et al. | 604/96 |
| 4,861,336 | 8/1989 | Helzel | 604/95 |
| 5,041,085 | 8/1991 | Osborne | 604/95 |

*Primary Examiner*—Fred C. Rosenbaum
*Assistant Examiner*—Chalin Smith
*Attorney, Agent, or Firm*—St. Onge Steward Johnston & Reens

[57] ABSTRACT

A fully automatic organ pressure sensitive apparatus for dislodging and removing obstructions in bodily cavities or organs by both delivering and removing fluid thereto, operable by high rate continuous or intermittent infusion of fluid solvent over a set pressure range to effect rapid dissolution and removal of the obstruction without complications to the patient. By continuous feedback monitoring of fluid pressure in the bodily organ or cavity of interest, the apparatus can constantly vary infusion and aspiration rates to maintain the set pressure range. If the pressure persists above or below the set range, the apparatus activates a safety feature leading to a period of maximal aspiration and cessation of infusion, followed by cessation of solvent transfer and triggering of an alarm to alert the operator.

15 Claims, 14 Drawing Sheets

CATHETER FOR CHEMICAL CONTACT DISSOLUTION OF GALLSTONES

This application is a continuation of application Ser. No. 07/482,194, filed Feb. 20, 1990, now abandoned which in turn was a continuation-in-part of application Ser. No. 07/180,099 filed Apr. 11, 1988, now U.S. Pat. No. 4,902,276, issued Feb. 20, 1990, which in turn was a continuation-in-part of application Ser. No. 06/871,775, filed Jun. 9, 1986, now abandoned.

BACKGROUND OF THE INVENTION

For most individuals who suffer from gallstones, the treatment of choice is to have a cholecystectomy, or surgical removal of the gallbladder. Each year 500,000 such operations are done in the United States alone. Recently, because of the cost, prolonged recuperation time and possible side effects associated with this surgery, methods have been developed for chemically removing gallstones in situ. Generally, this procedure involves inserting a catheter into the gallbladder followed by infusing a chemical solvent capable of dissolving the gallstone. The procedure thus avoids the need for and attendant risk of surgery.

A variety of chemical solvents have been tried and found to exhibit varying efficiencies of gallstone dissolution, depending on the chemical nature of the gallstone. Gallstones are generally composed of cholesterol or calcium salts, particularly calcium bilirubinate and calcium carbonate. Lipid solvents are effective at dissolving cholesterol gallstones, whereas these solvents have little or no solubilizing effect on gallstones composed of calcium salts. Thus, diethyl ether readily dissolves cholesterol gallstones, and other solvents such as mono-octanoin, and octadiol (glyceryl-1-octyl ether) also have good solubilizing properties. Unfortunately, few if any solvents are satisfactory for dissolving calcium gallstones. The invention herein will therefore find principal utility in cholesterol gallstone removal. It has been recognized that ether compounds such as diethylether have excellent cholesterol solubilizing properties, low viscosity and very good kinetic solubility but diethylether is hazardous since it boils below body temperature. Recently methyl tert-butyl ether (MTBE), a solvent hithertofore used primarily as a gasoline additive and a chromatographic solvent media, has been used for gallstone dissolution since it exhibits all the properties of ethers. Moreover, MTBE boils above body temperature and the solvent rapidly dissolves the gallstones without damaging the mucosa of the gallbladder.

The effectiveness of such new solvents has led to considerable activity focused on developing apparatus and methods for delivering MTBE and similar solvents to patients suffering from gallstones in ways to most rapidly and effectively solubilize gallstones without the complications arising from introducing such solvents into the body. (For brevity herein, the description will be with respect to use of the MTBE as a solvent. It will be recognized, however, that this invention will be applicable to a number of different solvents).

Physicians currently treat cholesterol gallstones by infusing MTBE into the gallbladder through a percutaneously positioned catheter through which MTBE is manually passed using glass syringes [Walker, *Lancet*, 1, 874 (1891); Shortsleeve, *Radiology*, 153, 547 (1984); and Teplick, *Radiology*, 153, 379 (1984)]. Additionally, physicians have available fixed volume syringe pumps, such as described in U.S. Pat. No. 4,655,744 to Thistle et al. to infuse and aspirate MTBE. There are several complications associated with either the manual infusion or the fixed volume pump-assisted infusion procedure.

When MTBE is delivered manually via glass syringes or with the aid of a fixed volume-cycle pump, spontaneous gallbladder contraction or over filling of the gallbladder cannot be detected or controlled. Consequently, MTBE periodically empties into the duodenum, producing duodenal mucosal injury, which in turn produces nausea, vomiting, duodenal erosions and accompanying pain of sufficient intensity to necessitate frequent administration of analgesics. In addition, when in the duodenum, MTBE can be absorbed into the blood stream, which in turn may result in somnolence or hemolysis and concomitantly the presence of the intense and irritating MTBE odor in the patient's breath.

Other problems associated with the manual or pump-associated syringe method involve inefficient removal of insoluble gallstone particles which constitute varying percentages of cholesterol gallstones. Such particles are often left behind in the gallbladder, after MTBE dissolves the cholesterol portion, in procedures involving syringes or syringe pumps. These particles often serve as the nidus for new gallstone formation. Additionally, both procedures are time consuming, laborious and require individuals that are highly skilled in their use. Consequently, the procedures are expensive because of the attendant costs associated with having a highly skilled staff of professional people to perform the procedure for prolonged times, often 12 hours or more. In addition, a fixed volume syringe pump can not prevent bile from entering the gallbladder during the course of its secretion by the liver. Bile in the gallbladder impedes the solvent's contact with stones and hence delays the process of dissolution.

It is obvious that delivering MTBE to a patient requires the utmost care to avoid releasing the solvent into the patient's bodily fluids or outside the area of treatment. Thus a key consideration in developing devices used in the chemical therapy of gallstone dissolution is ensuring the controlled delivery and removal of the solvent used to dissolve the gallstones. Considering that studies have shown that solvents such as MTBE are injurious if they pass into the intestine where they get absorbed, there is a critical need for devices that ensure that such chemicals will not be released during chemical therapy for gallstone removal. At the same time such devices must be able to maintain high solvent circulation rates into the gallbladder to create the necessary turbulence that will enhance dissolution and aid in evacuating the insoluble residue.

Also, because of the need to ensure containment of solvents, in addition to the safety features described above, a suitable device should be "user friendly" and not require the presence of highly skilled technicians to run the device. Further, for the same reasons, it should be easily maintainable.

With a little reflection, it becomes apparent that there are considerable hurdles to surmount if one is to develop a device that has the features described above. For instance, it must be "intelligent" and capable of sensing instantaneous changes in gallbladder pressure brought about by gallbladder contractions or by infusing the solvent, and rapidly relay this information to controlling feedback circuits. This is a crucial feature for such a device. If a gallstone should in some way prevent the necessary circulation of the solvent through the gallbladder, a critical pressure will build up, possibly rupturing the organ or causing leakage of the solvent from the gallbladder through the cystic duct into the common duct and intestine. Thus the device must be "intelligent" in the sense that it senses gallbladder pressure changes over a predefined range and reacts fast enough to keep the pressure in that range, shutting down or reacting appropriately if the pressure persists outside the range. Moreover, it would be desirable to have a device that not only is capable of shutting down, but actually can flush out any debris causing the blockage, and resume normal operation should the debris be removed. Such device should prevent intra-gallbladder pressure from rising above leakage limit and from falling below the pressure under which bile will be sucked into the gallbladder from the biliary duct.

SUMMARY OF THE INVENTION

The invention herein comprises an apparatus and a method for its use which are for therapeutic treatment of obstruc-tions in bodily organs by high rate solvent circulation, particularly for gallbladder or common bile duct stones. The apparatus has the desirable feature of continuous high rate infusion and aspiration while preventing solvent leakage from the bodily organ being treated. The apparatus comprises a forward or reverse acting solvent delivery means that is linked via a pressure transducer to a feedback controller circuit.

The apparatus is preset to perfuse within a set pressure range. Continuous feedback of true intraluminal organ pressure to a controller circuit via the transducer controls the rate and the net direction of solvent delivery by the apparatus and is determinative of whether the apparatus acts in the forward or reverse mode. Over this range the solvent is constantly passed from a reservoir into the gallbladder, and from the gallbladder it is aspirated to a suitable receptacle. Delivery and removal of the solvent is at a rate sufficient to effect gallstone dissolution and fragmentation, agitation and aspiration of insoluble fragments. Should there be an increase in pressure, a feedback loop switches the device into a high pressure mode, thereby diverting the solvent away from the gallbladder. If after a predetermined period of time the pressure sensing transducer readings from the gallbladder indicate a return to normal operating pressure range, the device automatically reinitiates the normal infusion and aspiration (perfusion) mode.

An additional feature of the invention is a self purging mechanism. After a preset interval, if the pressure does not decrease, the device enters a reverse mode to purge the aspiration port of the catheter, whereby fluid is aspirated backward through the infusion port and infused through the aspiration port to purge for discrete short intervals, during which time the pressure in the organ is continuously monitored. Once the blockage is removed by this "self-purging" action, the pressure transducer again indicates normal operating pressure, and the device resumes action in the normal pressure mode. However, should the obstruction not be removable after a predetermined number of purge cycles, an alarm circuit is activated, so notifying the user. A further feature of the invention is that it is able to distinguish clinically significant pressure changes occurring within the gallbladder which leads to emptying of gallbladder contents into the duodenum from those clinically insignificant changes arising as a result of coughing, laughing or like behavior. This feature prevents needless changes or operating modes.

A further aspect of the invention is a catheter for the contact dissolution of gallstones having a solvent infusion lumen and a solvent aspiration lumen in side-by-side relationship. The catheter is sized for introduction of its distal portion into the gallbladder from outside the body. Each lumen has at least one opening in the distal portion for communication between the gallbladder and a remotely located pump. A third lumen provides a means to continuously sense intra-gallbladder fluid pressure and to transmit an indication thereof to the controller, for control of infusion and aspiration of solvents via the lumens. An aspect of the invention is that the cross-sectional area of the aspiration lumen is larger than the cross-sectional area of the infusion lumen. Fluid moves into and out of each lumen by a series of openings in the walls of the catheter. The cross-sectional area of each opening is less than the cross-sectional area of the lumen with which the opening is in communication. The catheter further includes a retention means to prevent the catheter from being dislodged from the gallbladder. The retention means is a curved formation of the distal portion of the catheter. The pressure sensing means is located to lie at the inner radius of the curved formation to prevent its blockage by the mucosa of the gallbladder. Alternatively, the retention means may be an inflatable balloon located adjacent to the distal portion.

A tension string for holding the distal portion of the catheter in a curved configuration is included. The catheter also has a string passage lumen in which the string is located. Alternatively, the string may be located in either the aspiration lumen, the infusion lumen or the pressure sensing lumen.

The opening at the distal end of the catheter is in communication with the aspiration lumen. The catheter has at least one aspiration opening, in the wall of the catheter in communication with the aspiration lumen, which is located proximal to all infusion openings. The proximally-located aspiration opening is located adjacent to the point of entry of the catheter into the gallbladder when the catheter is in position for operation.

The lumen and aspiration opening at the distal end of the lumen are constructed and arranged to enable the catheter to pass over a guide wire. The catheter is made of material, for example polyurethane, which is resistent to the solvent to be infused into said gallbladder.

The means for sensing the pressure of fluid within the gallbladder includes a third fluid pressure transmitting lumen extending side by side with the infusion and aspiration lumens and having a distal opening in the distal portion of the catheter. The lumen is constructed to communicate intra-gallbladder pressure to a remotely located pressure transducer via a hydrostatic fluid column. The means for sensing the pressure of fluid within the third lumen comprises a pressure transducer located at the proximal portion of the catheter. Alternatively, the pressure transducer may be located at the distal end of the catheter and provide in situ gallbladder pressure measurements. Such transducers for in situ use can be piezoelectric, or fiberoptic, and may be removably inserted in a lumen of the catheter. The wires or fiber of an in situ transducer located at the distal end of the catheter can pass through the pressure lumen, infusion lumen, or aspiration lumen or may be embedded into the catheter's wall. The catheter has a structural formation at its proximal end that permits it to be used only with a solvent delivery system having a predetermined mating structural formation that prevents inadvertent use with non-mating systems. Alternatively the catheter has an electrical or fiberoptic connection at its proximal end that permits it to be used only with a solvent delivery system having a predetermined electrical or fiberoptic connection.

One aspect of the invention is a microprocessor programmed to execute an algorithm in response to an input pressure signal derived from the gallbladder through a pressure determining module; a pump control module, to control the speed and direction of an infusion pump pumping solvent through an infusion lumen into the gallbladder of the patient and an aspiration pump pumping solvent through an aspiration lumen out of the gallbladder of the patient; and a response determination module to control the functions of the pump control module in response to the pressure determinations of the pressure determining module. The response determination module generates an alarm and initiates maximal continuous aspiration by both infusion and aspiration pumps in response to a number of intra-gallbladder pressure conditions including: no pressure variations of a predetermined amplitude detected for a predetermined period of time; abnormal pressure detected for a predetermined period of time or after predetermined volume has been used to purge said aspiration lumen; more than a predetermined number of purge cycles occurring within a predetermined period of time; detected pressure remaining less than a lower set limit for a predetermined period of time or the system being unable to maintain the pressure within normal range for a predetermined period of time.

The response determination module also stops infusion and maintains aspiration in response to intra-gallbladder pressure exceeding an upper set limit and aspirates through the infusion lumen until the pressure falls to an acceptable range. The response determination module then reverses flow to purge the aspiration lumen. The module also stops aspiration in response to the condition wherein the pressure is less than the lower set limit.

Another aspect of the invention is a means for continuously measuring the pressure within the gallbladder of a patient and a means for controlling the infusion and aspiration of a solvent into the gallbladder in response to those measurements to maintain said pressure within the set limits.

A further feature of the invention is a method for dissolution of gallstones comprising the steps of continuously measuring the pressure within the gallbladder of a patient and controlling the infusion and aspiration of a solvent into the gallbladder in response to those measurements. The method further comprises the step of periodically measuring the amount of cholesterol in the solvent and replacing the solvent when the cholesterol concentration in the solvent reaches a predetermined concentration limit.

The method further comprises, prior to introduction of solvent into the gallbladder, the measuring of a critical leakage pressure at which fluid in the gallbladder discharges into an adjacent part of the body, and using the value of that pressure for controlling the infusion and aspiration. The step of measuring the critical leakage pressure comprises the injection into the gallbladder of a radiopaque dye at increasing pressure until the discharge of the dye is observed radiographically. The amount of pressure required to cause the leakage of dye is recorded as the critical leakage pressure and the amount of fluid required to fill the gallbladder is the available volume. The step of infusing the solvent into the gallbladder occurs at a rate sufficient to create solvent turbulence adjacent the gallstones.

An aspect of the invention further includes a system, including a system bus; a microprocessor in communication with the system bus; a memory for holding algorithms, the memory in communication with the system bus; an analog to digital converter having an input terminal for receiving an analog signal representative of the intra-gallbladder pressure and an output terminal for applying digital signals representing the pressure on said system bus; a pressure transducer having a pressure sensor and an output terminal, the output terminal of the pressure transducer in communication with the input terminal of the analog to digital converter. The pressure transducer generates a pressure signal related to the pressure of the solvent within the gallbladder.

The system also includes a reservoir, for filling with a gallstone dissolving solvent, an infusion pump connected by conduits to pump solvent from the reservoir into the gallbladder, and an aspiration pump connected by conduits to withdraw solvent from the gallbladder and discharge the solvent back into the reservoir. The system further includes a pump controller having an input terminal in communication with the system bus and a plurality of output terminals, one of said output terminals in communication with the aspiration pump and one of said output terminals in communication with the infusion pump, the microprocessor controlling said pump controller, which in turn controls the aspiration and infusion pumps in response to signals received from said pressure transducer. The microprocessor terminates infusion and initiates aspiration in response to signals indicating excess pressure in the gallbladder.

Additionally, the system also includes a catheter having a plurality of lumens, a first one of the lumens connected at its proximal end to the infusion pump; a second one of the lumens connected at its proximal end to the aspiration pump; and a means to sense intra-gallbladder fluid pressure associated with the distal portion of the catheter for continuously providing an indication of the pressure of fluid to the pressure transducer.

Yet another aspect of the invention is the ability to safely dissolve gallstones when pressure measurements are uncertain by infusing and aspirating continuously a volume of solvent which is less than the available volume of the gallbladder.

BRIEF DESCRIPTION OF THE DRAWINGS

FIG. 9A is a cross-sectional view of the catheter of FIG. 9 taken through line 9A—9A.

DETAILED DESCRIPTION OF THE INVENTION

Figure 1:
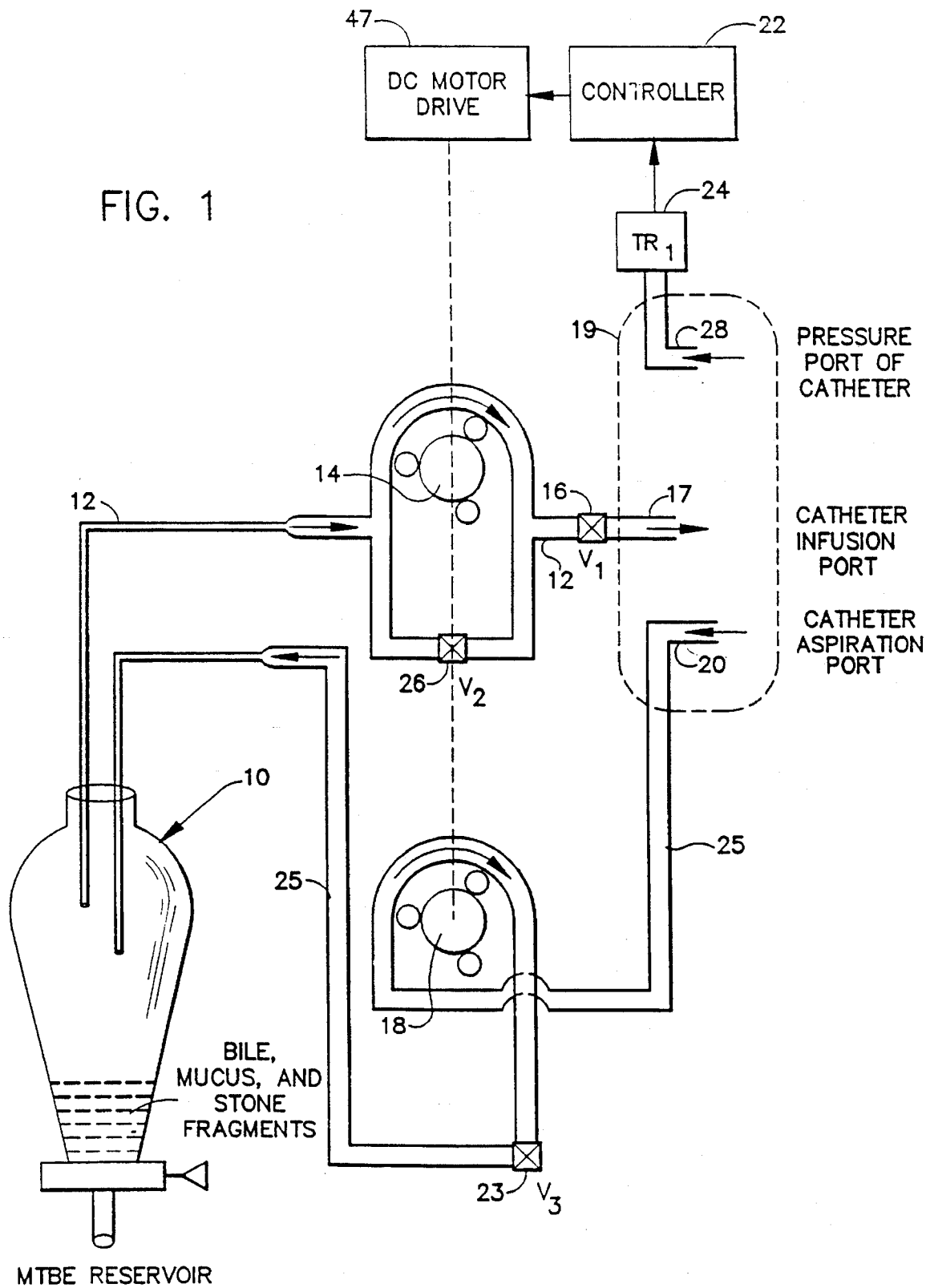
FIG. 1 is a schematic diagram of an apparatus suitable for delivering solvent to a gallbladder and for removing the solvent containing dissolved or fragmented gallbladder stones.

The invention described herein is suitably employed for delivering fluids (solvents) to organs for removing obstructions contained therein. It will be appreciated at the outset that, while the subject invention described below details the invention regarding the removal of gallstones from the gallbladder, the invention can be used to remove a variety of obstructions from bodily cavities or organs other than the gallbladder, and thus should not be construed as being narrowly limited to the treatment of gallstones. Indeed, it will become readily apparent that the device is easily adapted to removing obstructions from organs or bodily cavities in general.

The invention described herein is an organ pressure sensitive apparatus having a solvent delivery means in constant communication with a controller circuit via one or more pressure transducers that monitor the intra-organ pressure.

The pressure transducer may be positioned either within the gallbladder itself or external to the patient at the proximal end of a fluid filled column whose distal end is placed within the gallbladder. This can be accomplished by using the pressure sensing lumen either as the fluid filled column or as the in situ location of the pressure sensing transducer itself. A variety of pressure transducers are available for both in situ and fluid column use. In situ transducers need be small and capable of withstanding the effects of the solvent. Suitable transducers include but are not limited to fiber optic pressure sensors, piezoelectric pressure sensors and capacitative sensors. The wires or fibers of an in situ transducer pass through the separate pressure sensing lumen or through either of the solvent flow lumens or may be embedded in the catheter wall. A suitable transducer for use on the proximal end of the fluid column is a Statham Gould pressure transducer P23ID. When using an in situ transducer, it is possible to have the transducer removable from and insertable into the catheter once the catheter is in position within the gallbladder. In this way, the transducer can be replaced during the procedure. Additionally, such an insertable transducer would permit the use of a smaller catheter for the same amount of fluid flow since it could be placed in one of the flow lumens. The apparatus functions over a preset pressure range delivering fluid to the gallbladder, causing the fluid to contact and dissolve the gallstones, and withdrawing fluid from the gallbladder, thereby accomplishing the removal of dissolved or fragmented gallstones. The rate of solvent delivery and removal can be adjusted to create the necessary turbulence to dissolve or fragment gallstones. If the pressure exceeds that of the normal operating range, the apparatus diverts solvent from the organ, thereby preventing leakage of the solvent from the site of treatment. Further, above the normal operating pressure range, the apparatus can be programmed to be "self-purging". This may be desirable in the instance when the obstruction is only partially dissolvable, causing blockage of the solvent removal or aspiration means. At pressures below the normal operating pressure range, the rate of aspiration is decreased while infusion continues, thereby reestablishing normal operating pressure.

Dissolution time is minimized by operation at high solvent flow rates. The maximum flow is attained when the instantaneous infusion flow matches the instantaneous aspiration flow. At such a null point, neither pump is slowed down or shut off by the pressure determining algorithm. A feature of this invention is the calibration of the pump catheter system in both infusion and aspiration, hence generating a flow vs. control voltage relationship for both pumps. An input parameter is the desired flow rate. The microprocessor will not accept values which can not be attained by both pumps and operates both pumps at the desired flow rates when the pressure is in the vicinity of the pressure set point. As pressure rises above the set point the aspiration pump speed is increased and as the pressure falls below the set point the aspiration pump speed decreases thus possessing an ability to drive the system to the set point. During a procedure, the flow rate may be increased to a value limited by either the aspiration, or infusion lumen, or the size and compliance of the patient's gallbladder and/or the attendant pressure excursions experienced.

A key consideration with regard to the organ pressure-sensitive aspects of the system is the realization that leakage of solvent from the gallbladder occurs when the intraluminal pressure exceeds that in the cystic duct, common bile duct or ampulla (whichever is selected for the procedure in a particular patient) and that neither the gallbladder volume per se nor the flow rate of solvent per se are intimately involved. This in turn leads to recognition that critical leakage pressure from the gallbladder differs from patient to patient, and that leakage is a function not only of solvent delivery but natural gallbladder contractions or external pressures to the gallbladder. The subject invention takes into account those pressure changes that are of sufficient duration or strength to affect solvent leakage.

Because the critical leakage pressure from the gallbladder differs from patient to patient, it is important to determine the critical leakage pressure for each individual patient. To determine this pressure, a catheter is introduced into the gallbladder and, under fluoroscopy, a contrast material is injected into the gallbladder with increasing pressure. The pressure at which the contrast medium enters the intestine or leaks at the percutaneous entry point is the critical leakage pressure. As the gallbladder fills, its pressure will increase until contrast medium is observed radiographically to flow through the cystic duct into the common bile duct or leak at the percutaneous entry site. The volume of dye present in the gallbladder at this pressure is the available volume. This critical leakage pressure, or a safety pressure below the critical leakage pressure, and, if desired, the available volume are entered as parameters in the controller. From the critical leakage pressure value, the high pressure or maximum operating point or upper set limit is determined.

Typically, the maximum operating pressure is set at 75% to 90% of the measured critical leakage pressure, and the maximum pressure alarm is typically 85%–95% of the critical leakage pressure.

To determine the minimum operating pressure or lower set limit, the contrast medium is aspirated from the gallbladder. As the pressure inside the gallbladder falls, bile will eventually begin being aspirated into the gallbladder from the common bile duct. The pressure at which this occurs is the bile aspiration pressure. The minimum operating pressure or lower set limit is typically set 2 to 10 cm of water above the bile aspiration pressure to minimize solvent dilution with bile. The minimum alarm pressure is set slightly below the bile aspiration pressure.

Since the amount of fluid retained within the gallbladder is measured by determining the amount of fluid infused and the amount of fluid aspirated this volume value can be used as a safety check on the system. When the amount of fluid retained within the gallbladder approaches the available volume of the gallbladder an alarm is set. The monitoring of the retained volume is especially important in the case where accurate pressure measurements are not possible, for example, due to the number and volume of stones within the gallbladder. Such accurate and continuous volume measurements permit the system to be used safely when the pressure values are in doubt.

FIG. 1 shows an exemplary apparatus for removing gallstones. Reservoir 10 contains a solvent that is a chemical suitable for dissolving gallstones. Should the gallstone be composed of cholesterol, a variety of solvents would be efficacious. Particularly effective is methyl tert-butyl ether (MTBE). The latter has been shown to readily dissolve cholesterol stones rapidly both in vitro and in vivo. At normal operating pressures, the solvent moves via a conduit 12 from the reservoir 10 by aid of a first pump 14. The fluid then moves through a valve 16 and from the valve through infusion port 17 in a catheter 19 into the gallbladder. During this operation valve 26 is closed to prevent solvent return to reservoir. The solvent is delivered at a predetermined effective rate for gallstone dissolution thereby providing solvent turbulence and contact with the gallstones for a period of time sufficient for effective gallstone dissolution or fragmentation and fragment removal.

Simultaneously with the delivery of MTBE to the gallbladder, a second pump 18 aspirates the fluid from the gallbladder now containing dissolved gallstones and debris. This material passes out of the gallbladder via an aspiration port 20 in the catheter. The fluid is pumped from the gallbladder by pump 18, passing through valve 23, and from there it is deposited in a receiver reservoir. Either reservoir 10 used as the source of the solvent or a separate reservoir is suitable for this purpose. FIG. 1 shows the same reservoir 10 being utilized as both the source of fluid passed to the gallbladder and as the receiver of aspirated fluid therefrom. It is worth noting that if the same reservoir is used, gallbladder stone fragments, bile, mucous and the like removed from the gallbladder are heavier than the solvent, MTBE, and therefore settle to the bottom of the reservoir and do not hinder continued withdrawal of essentially pure fluid from the reservoir to effect further stone dissolution.

In the case where a single reservoir is used to supply the solvent and receive the aspirated fluid, the fluid should be periodically sampled and the cholesterol concentration in the MTBE measured. Since the heavy debris falls to the bottom of the reservoir, the sample of the fluid should be taken of the fluid from the upper portion of the reservoir. The sample can then be tested to determine the cholesterol concentration level, for example by spectrophotometry. The fluid should be removed and replaced when the cholesterol concentration reaches a predetermined level (e.g. about 30%). It should be noted that higher or lower concentration levels of cholesterol in the solvent only effect the efficiency of dissolution.

Further, in a single reservoir system, since the aspiration rate and the infusion rate are in general not equal, there is a provision to vent the reservoir. The venting method should not allow the flammable fumes of the solvent to escape. An alternative way of compensating for rate differences is the use of a solvent resistant bladder for the reservoir. Such a bladder expands or contracts as the volume of fluid contained within it changes. This form of closed reservoir prevents fumes from escaping.

The pumps 14 and 18 are controlled by a controller circuit 22. The controller circuit 22 in turn receives pressure readings from the transducer 24 causing the controller circuit 22 to open or close flow valves 16, 23 and 26 to inhibit infusion or aspiration as necessary to control organ pressure depending on whether the transducer 24 indicates that the pressure in the gallbladder is within, above, or below the normal operating pressure range. The transducer in turn senses the gallbladder fluid pressure by communication through port 28 of the catheter 19.

At the normal operating pressure, first pump 14 delivers fluid from reservoir 10 through tube 12 and valve 16 to the gallbladder. Simultaneously, and at a slightly slower rate, second pump 18 aspirates the fluid from the gallbladder through catheter aspiration port 20. Fluid passes through the valve 23 and thence through conduit 25 to the reservoir 10.

Conduit 12, catheter 19 and conduit 25 form a fluid circuit connecting the source reservoir 10 with the bodily organ or cavity into which the catheter is inserted and then to the receiving reservoir (which as noted may also be reservoir 10). The pumps 14 and 18 are in the circuit, in conduits 12 and 25 respectively. (For the purpose of description herein, the "forward" fluid flow direction will be defined as flow in the direction of the arrows in FIGS. 1 and 6, and "reverse" flow will be flow in the direction opposite the arrows.)

The controller 22 is programmed to respond to pressures that exceed or are below that of the normal operating pressure range. Above the normal operating pressure range ("high pressure mode"), the controller 22 shuts down valve 16 and simultaneously opens valve 26. This provides a path for diverting the incoming fluid away from the gallbladder. At that time valve 23 is open to continue gallbladder emptying to return the pressure to the normal operating range. If the pressure in the gallbladder does not return to the normal operating pressure setting within a preset time, for example a few seconds, then the controller 22 can be programmed to instruct the pumps to reverse the direction of fluid movement, and simultaneously valves 23 and 26 are closed. The controller unit is programmed to close valve 23 after a slight delay so that a small amount of fluid, approximately 1 ml, can pass through the valve before it is shut. Valve 16 is opened to provide a path for fluid to be reverse aspirated from the gallbladder in this "self-purging" mode. This mode essentially causes a small amount of fluid to be pumped in through the aspiration port 20 of the catheter 19 to clear it of obstructions while aspiration is effected by pump 14 through valve 16. The fluid which is pumped into the gallbladder passes from the reservoir 10 through valve 23, prior to valve 23 closing in response to high pressure present in the gallbladder. Generally this will consist of about 1 ml of fluid passing through valve 23 before it shuts. This mode of operation continues for a brief period of time, and then the controller unit 22 instructs the machine to resume normal operation should the obstruction be removed and the pressure transducer 24 indicate reestablishment of the normal operating pressure range. If the transducer continues to indicate pressures present in the gallbladder above the normal operating pressure, the controller unit 22 again instructs the pumping apparatus to purge the system. If, after several "self purging" cycles, the obstruction is still not removed, the controller unit 22 then shuts down the system and activates an alarm circuit 34 notifying the user of a potentially dangerous condition.

Figure 2:
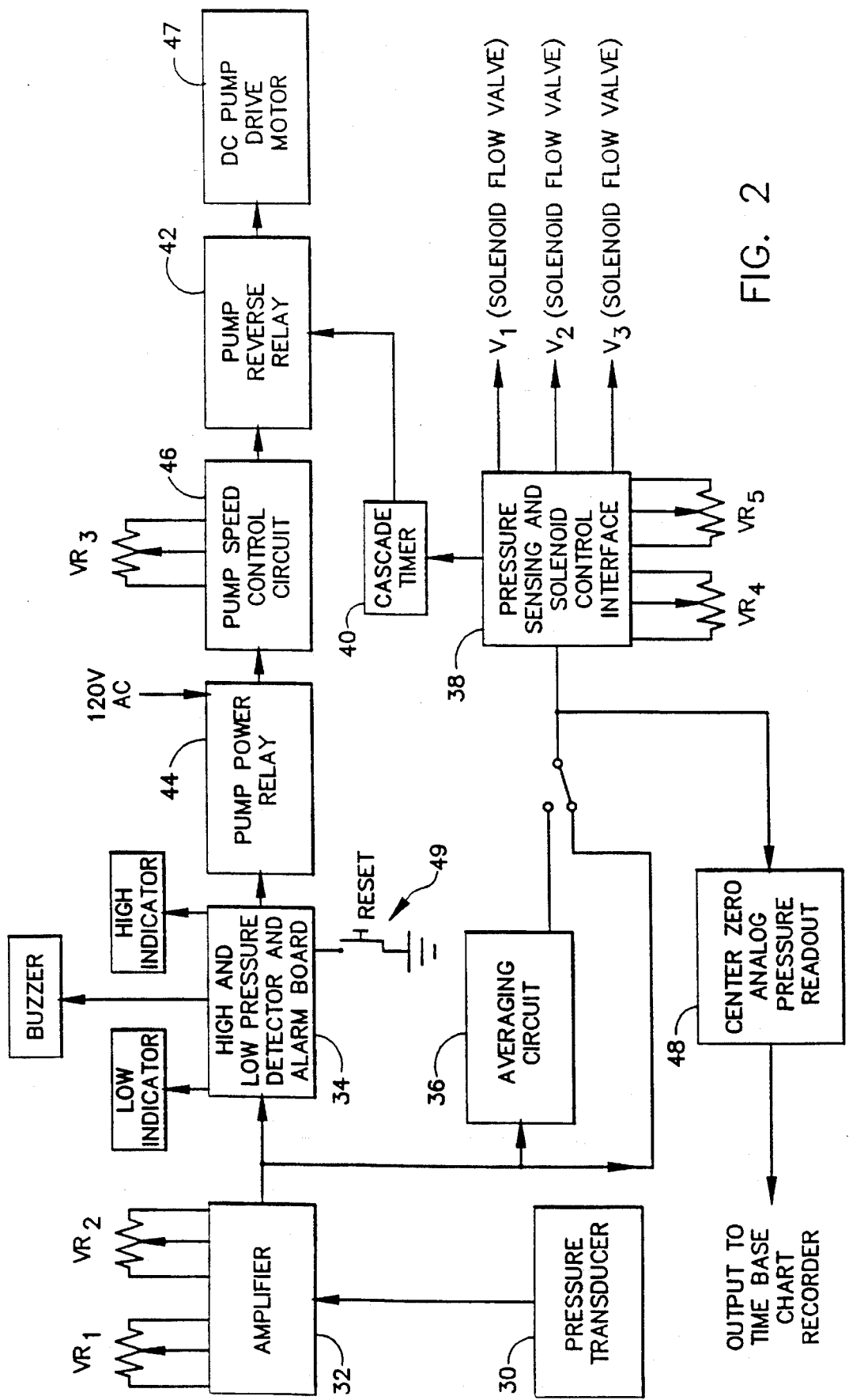
FIG. 2 is a schematic diagram of a controller circuit that regulates the pump units shown in FIG. 1, as well as other features of the apparatus.
Figure 3:
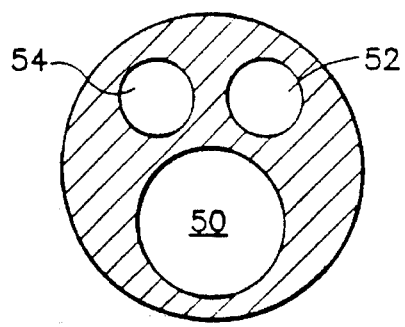
FIGS. 3, 4 and 5 show features of a three-lumen catheter, FIG. 3 being a sectional view taken on line 3—3 of FIG. 4.

FIG. 2 illustrates a representative controller unit 22. The controller circuit 22 instructs the pumps 14 and 18 to deliver or aspirate fluid from the gallbladder. Thus, a circuit will typically have a pressure transducer 30; such as the Statham Gould pressure transducer P23ID, as mentioned previously. The pressure transducer 30 relays information to an amplification device 32 which amplifies the signal from the transducer 30 and transmits it to a high and low pressure alarm circuit 34, then either directly or through the averaging circuit 36 to a pressure-sensing circuit 38 that reads preset low and high pressure values and which is connected to the valves 16, 23 and 26. The latter valves are typically solenoid flow valves or tube compression valves. The averaging circuit 36 can be switched in if desired to discriminate between pressure changes in the gallbladder arising from fluid build-up due to obstructions or from hyperventilating, laughing or like activities. Thus the averaging circuit essentially screens out artificially high or low pressure peaks which in fact do not lead to gallbladder emptying.

The pressure sensing circuit 38 is connected to a cascade timer 40, which in turn is connected to a pump reverse relay circuit 42. Thus, when gallbladder pressure exceeds that of the normal operating pressure range and the obstruction is not removed within a predetermined period, the cascade timer 40 activates the pump reverse relay 42. The latter circuit is responsible for "self-purging" the system. Should high pressure persist after several brief "self purging" cycles, then the alarm circuit 34 is activated, causing an initial period of aspiration in the reverse mode (with valves 16 and 23 open and valve 26 closed), then stopping the pumping system by shutting off its power supply and the triggering of a visual, audible or other alarm notifying the user. Note that at any time during the pump reverse cycle, should the pressure return to within the normal pressure range, the apparatus resumes normal operation.

It will be further noted as shown in FIG. 2 that a pump power relay circuit 44 and a pump speed control circuit 46 are also interactive with the whole system. The pump speed control circuit 46 derives power through the pump power relay 44, which, in turn, is controlled by the alarm circuit 34. The pump motor derives its power supply from the pump power relay 44. Any time an alarm condition exists, this relay shuts off power to the pump, stopping it from pumping. The pump speed control circuit 46 has a manual adjustment capability through which the operator can set the desired perfusion rate for that specific situation. An analog pressure read-out 48 is provided for the operator to assess effective operation and to refer to during calibration. Alternatively, or in addition, the output can be fed to a video display terminal 118 (of FIG. 10) driven by appropriate software to provide the operator with an intermittent or continuous display of system operating mode, pressure, etc., and may be integrated with the indicators and alarm of alarm circuit 34.

Figure 10:
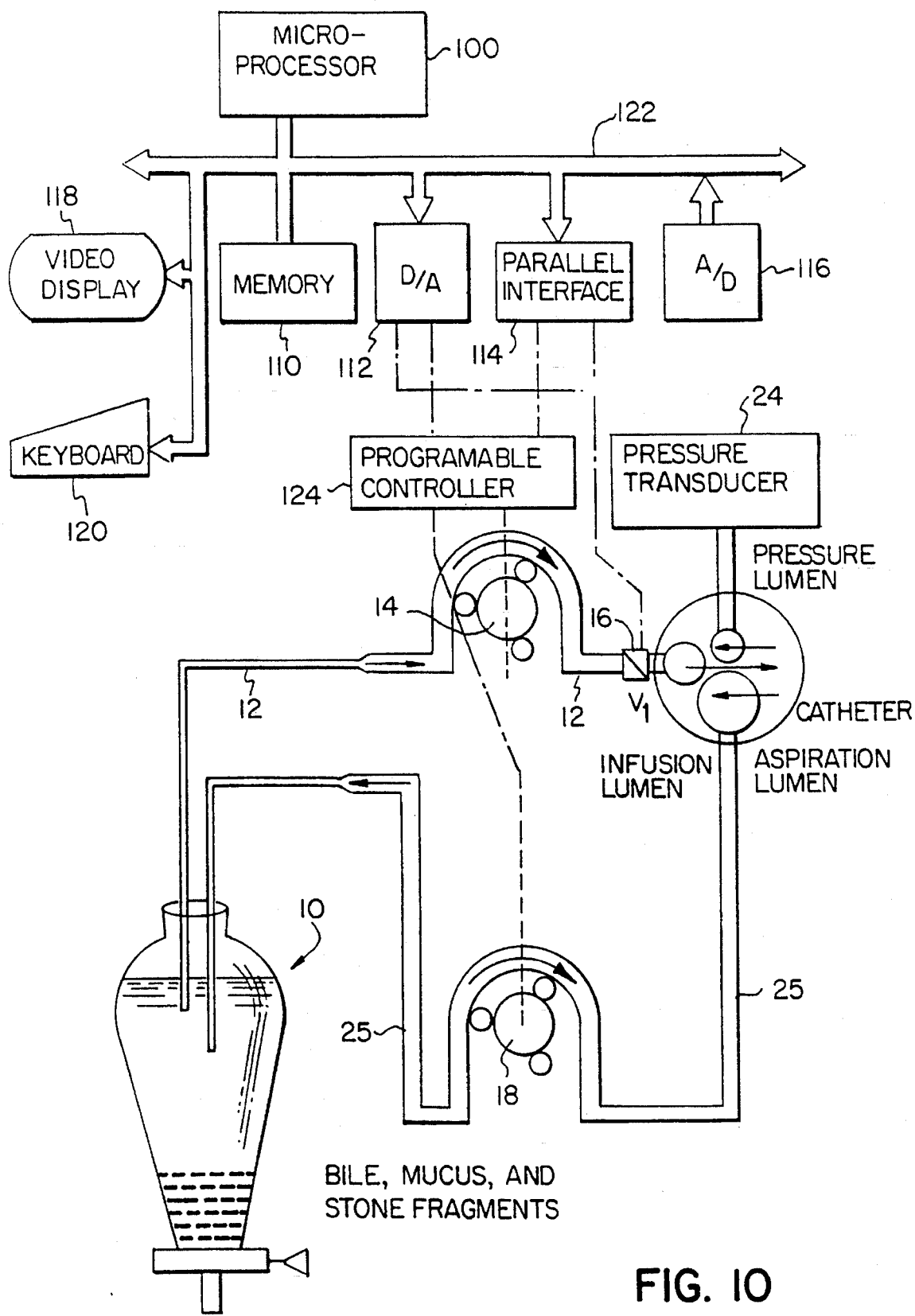
FIG. 10 is a block diagram of an embodiment of the apparatus wherein a microprocessor controls the components of the apparatus.

Note that if desired, one or more appropriate microprocessors can replace many of the components of the system. Referring to FIG. 10, in a system controlled by a microprocessor 100, the microprocessor 100 is connected to the pressure transducer 24 by an analog to digital converter (A/D) 116 connected to the system bus 122. The A/D converter 116 changes the pressure transducer's 24 analog signals to digital signals for processing. Control of the pumps is accomplished by the microprocessor 100 through a digital/analog converter (D/A) 112, if the pump controller (PC) 124 requires analog signals, or through a digital parallel or serial interface (P/SI) 114 if the pump controller 124 is capable of responding to digital signals. The D/A 112 or the P/SI 114 can also be used to control the solenoid valves 16 (only one shown for purposes of illustration).

The digital data is processed by the microprocessor 100 which executes algorithms located in memory 110 to perform the functions otherwise performed by components of the pressure sensing circuit shown in FIG. 2. Specifically, the microprocessor 100 by itself replaces the high and low pressure detector 34, the signal averager 36, and the cascade timer 40. The microprocessor 100 in conjunction with the A/D converter 116 replaces the pressure sensing portion of the pressure sensing and solenoid control interface 38, while the microprocessor 100 in conjunction with the D/A 112 or P/SI 114 replaces the solenoid portion of the pressure sensing and solenoid control interface 38. Further, depending upon the form of the controller 124 actually controlling the pumps 14, 18, the microprocessor 100 and A/D 116 or P/SI 114 also may replace the pump power relay 44, speed control circuit 46, and pump reverse relay 42.

Figure 6:
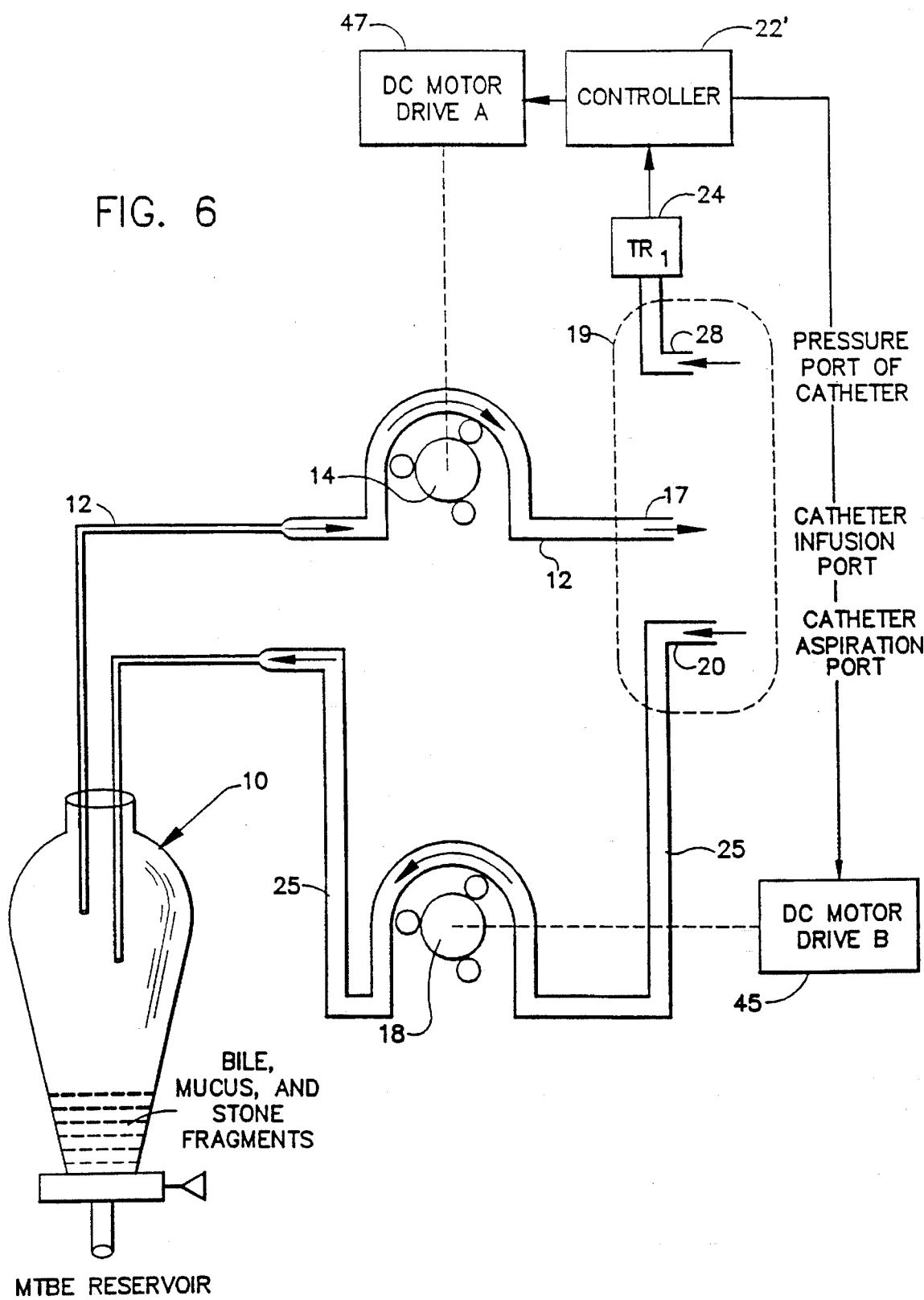
FIG. 6 is a schematic diagram of another embodiment of the apparatus.

FIG. 6 illustrates another alternative embodiment of the apparatus, which eliminates the valves by having separate control of the two pumps 14 and 18. Each pump motor has its own DC drive 47 and 45 respectively. Both drives are controlled by controller 22', which has an appropriate microprocessor to control the speed of each motor (and thus the flow rate of each pump) in response to the pressure signals from transducer 24. Thus instead of opening and closing valves to effect the proper infusion, aspiration or purging, the controller 22' regulates each pump's flow rate and direction of flow.

This embodiment has the advantage that all fluid conduits (tubing, catheter, reservoir) can be made of easily replaceable material. Thus each patient can be treated using a system in which all wettable surfaces are limited in use solely to that one patient and one treating session. Again many of the components of this embodiment can also be replaced with a microprocessor system.

There are several features of the apparatus that enhance its performance. The pumps preferred in the subject invention are peristaltic pumps. This type of pump offers several advantages such as the replaceable wettable surfaces mentioned above, which in addition to their individual sterility will be particularly advantageous in those instances where the solvent being used to dissolve the obstruction is at all corrosive. Moreover, peristaltic pumps are resistant to clogging, in contrast to standard syringe type pumps. However, it should be noted that syringe pumps are similarly employable in the subject invention in those instances where the fluid used to dissolve and remove the obstruction is a solvent, provided that the syringe pumps are constructed of suitable material, preferably polytetrafluoroethylene (PTFE) or glass. Syringe pumps made of plastic are not preferred in instances where the solvents used are incompatible with the plastic composition of the syringe. An additional disadvantage associated with the use of syringe pumps that is not present in peristaltic pumps is that in those instances where a solvent is being utilized, evaporation of the solvent from between the plunger and the body can cause deposits in the body of the syringe, causing it to "freeze" and thus interrupt delivery of the fluid to the organ being treated. Lastly, peristaltic pumps are capable of much greater fluid circulation rates than are syringe pumps. This is advantageous in certain instances where the obstruction to be removed, such as a gallstone, requires turbulent flow rates across the surface of the gallstone to accelerate the dissolution process.

A predetermined normal operating pressure range is programmed into the controller circuit 22. Should the pressure in the gallbladder exceed normal operating pressure, the action of the controller circuit 22 prevents leakage of solvent from the gallbladder through the cystic duct into the common duct, as well as into the intestine or around the entry site of the catheter. Also, because the controller circuit "sees" true gallbladder pressure, it readily adjusts to decrease as well as increase pressure by adjusting the net delivery rate of the solvent to the gallbladder. For example, should the pressure fall below the normal operating pressure range, the controller circuit 22 ceases or slows down the rate of aspiration of solvent, and simultaneously continues infusing solvent to reestablish normal operating pressure.

The pressure sensitive alarm circuit 34 is constantly comparing the system's set operating pressures and the gallbladder pressure. If gallbladder pressure cannot be brought into the normal operating pressure range by the action of the controller circuit 22 in a specified period of time, it will revert to a period of maximal aspiration, then shut down the pumping system and sound an alarm drawing the attention of the operator. The operator, after correcting the problem, can resume normal operation by activating the reset button 49.

Figure 12:
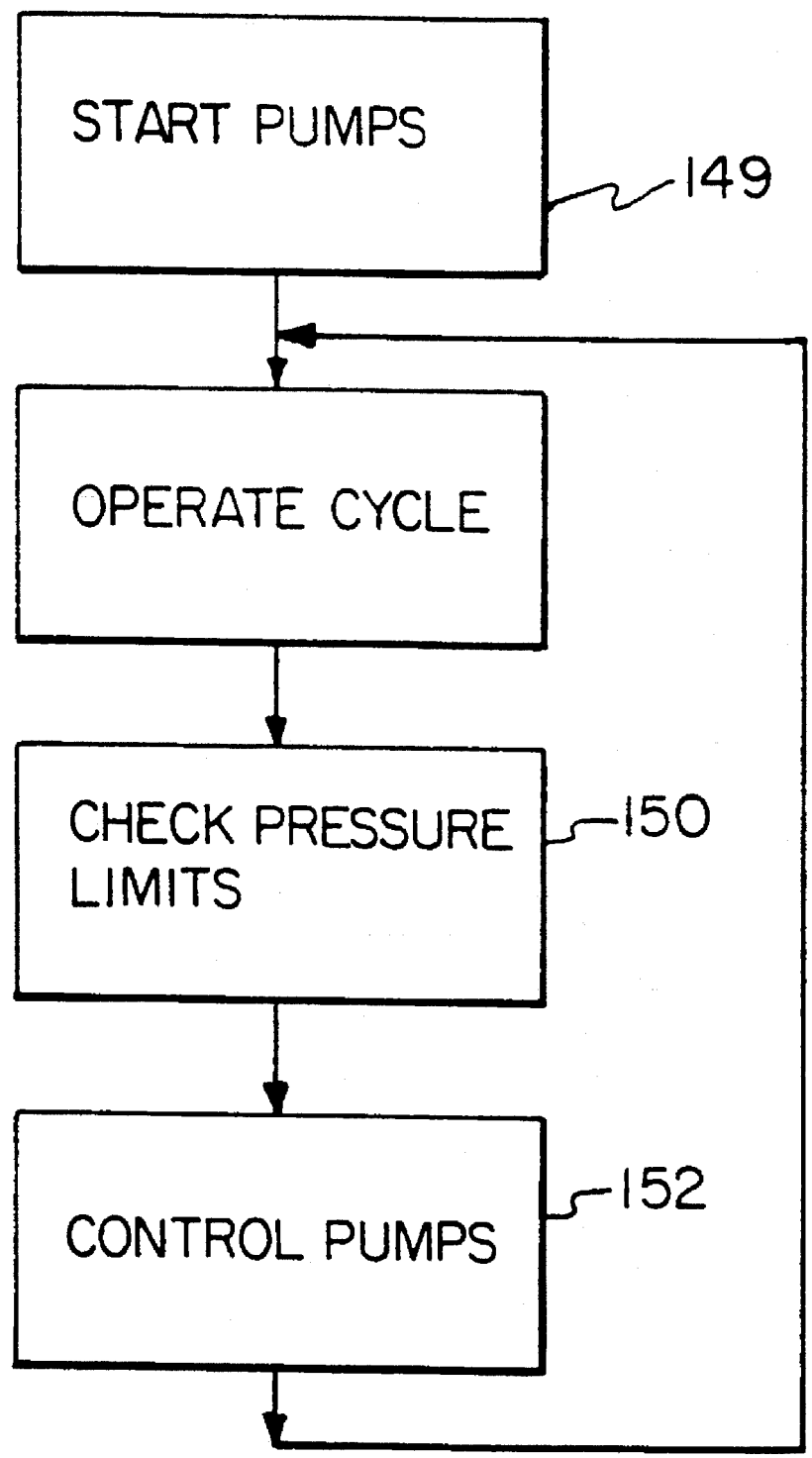
FIG. 12 is a flow diagram of an embodiment of the algorithm of the invention depicted in FIG. 10.

Referring to FIGS. 10 and 12, in the case of a microprocessor system, the microprocessor 100 monitors the pressure values produced by the transducer 24 and controls the pumps 14, 18, and valves 16 in response to those pressure values according to an algorithm stored in the system memory 110. The algorithm can be generally partitioned into a module for periodically making pressure measurements, a module for controlling pump speed and direction and a module for determining the proper response to the various pressure measurements.

The module for determining the proper response to the various pressure measurements checks several conditions. If there are no variations of a predetermined amplitude in the measured pressure for a predetermined amount of time, the module assumes that either the pressure lumen is blocked or that the pressure measurement subsystem has failed and sets an alarm condition. The setting of an alarm condition causes the pump control module to set maximal continuous aspiration by both pumps and to sound an alarm.

If the pressure measured is greater than the upper set limit, the pressure measuring module instructs the pump control module to stop the infusion pump and cause the aspiration pump to maintain aspiration. If the pressure continues to remain above the upper set limit for more than a predetermined amount of time, the module assumes that there is a blockage in the aspiration openings or lumen. In response to this condition, the pump control module instructs the pump normally used for infusion to aspirate. When the pressure falls to the lower set limit, the pump control module instructs the pump normally used for aspiration to switch to infusion and the pump normally used for infusion to switch to aspiration in an attempt to purge the side holes and lumen. If the operating pressure does not return to normal within a predetermined amount of time or after a predetermined volume has been used to purge the aspiration openings and lumen, an alarm condition is set by the response determination module. Further, if there are more than a predetermined number of purge cycles within a predetermined period of time, the response determination module sets an alarm condition.

If the pressure measured is less than the lower set limit, aspiration is stopped, and if the pressure remains less than the lower set limit for a predetermined amount of time, an alarm condition is set. Finally, if the system is unable to operate within its normal range for a predetermined amount of time, an alarm condition is also set.

FIG. 12 is a flow diagram of the main program loop of an embodiment of the algorithm used to determine the proper response to various pressure measurements. FIGS. 12A—12E are flow diagrams of subroutines executed during the main program loop. The main program calls the CHECK-PRESSURE-LIMITS subroutine 150 which in turn calls a series of other subroutines to perform specific functions when the pressures and/or time delays are outside the desired ranges, and when the pressure is above the upper pressure limit or below the lower pressure limit. Within the desired pressure range, the CONTROL PUMPS subroutine 152 operates the pumps in a proportional fashion in an attempt to stay within the pressure limits. The main program begins by the operator entering the operating parameters (operating pressures, alarm pressures, etc.) into the system by the system keyboard and then calling the START-PUMPS subroutine 149.

Figure 12A:
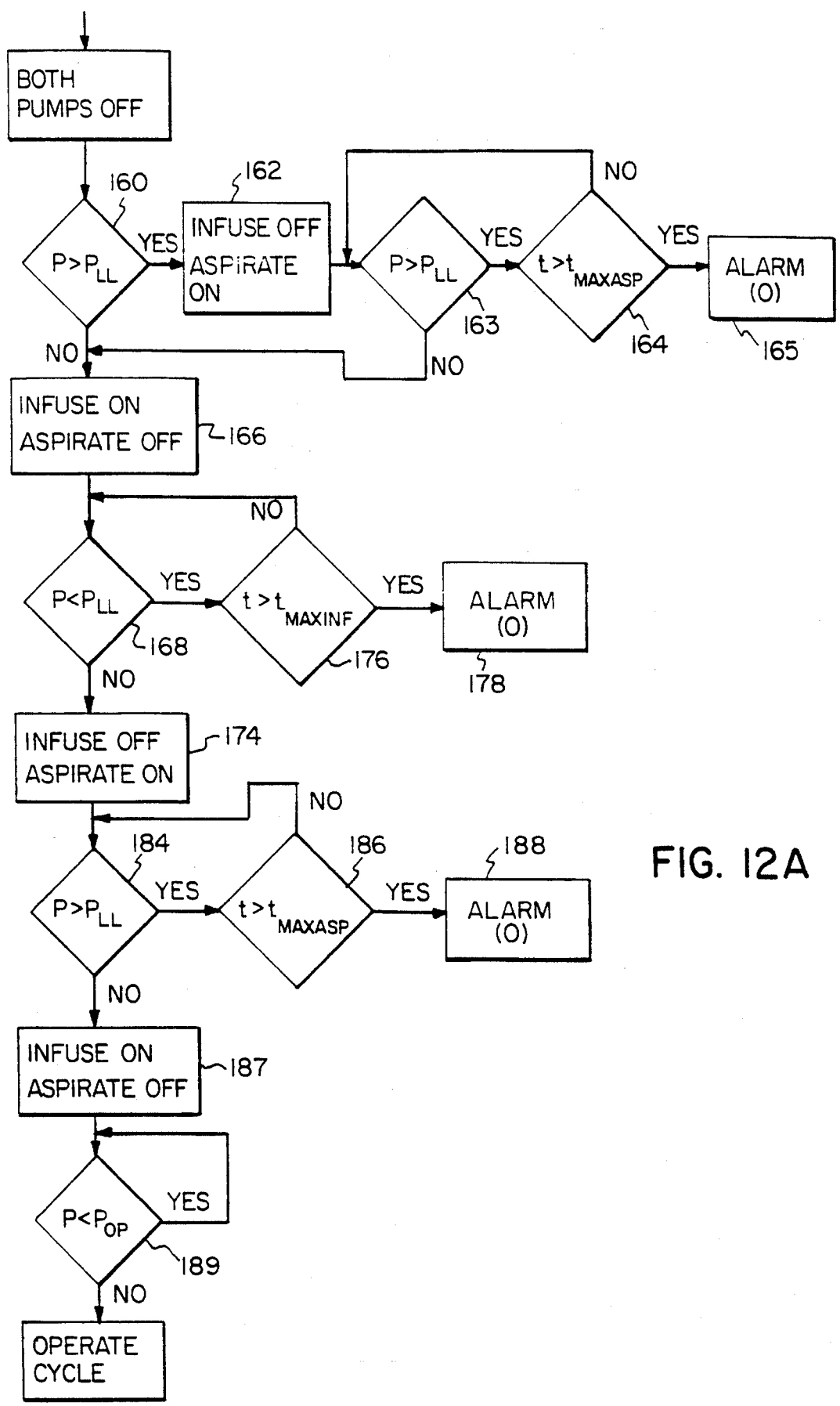
FIG. 12A is a flow diagram of the start pumps subroutine of the algorithm of FIG. 12.

When the main program is executed for the first time during the procedure, or when the pumps have been stopped and must be restarted the subroutine START-PUMPS is called. Referring to FIG. 12A, the purpose of the START-PUMPS subroutine is to determine from the present pressure measurement which pump should be started. That is, if the pressure is high initially, only aspiration should occur, while if the pressure is low only infusion should occur. Further, should the system be unable to come to the proper pressure operating range within a fixed amount of time, an alarm condition exists and the operator should be notified. To accomplish this, the subroutine begins by determining if the pressure in the gallbladder is greater than the lower operating pressure limit 160 and if the pressure is not greater, then the infusion pump is turned on and the aspiration pump remains off 166. If the pressure is greater, the infusion pump remains off, the aspiration pump is turned on 162, an aspiration timer is started, and the pressure is compared to the lower operating pressure limit again 163. If the pressure is still above the lower operating limit 163, the elapsed time from the start of aspiration as indicated by the aspiration timer is compared 164 to the maximum aspiration time allowed parameter. If the elapsed time is less than the maximum aspiration time allowed, the pressure is again compared with the lower operating pressure limit 163. If the elapsed time is greater than the maximum allowed then aspiration has failed to reduce the pressure and the alarm subroutine is called in an alarm (0) condition 165.

If the pressure is below the lower operating pressure limit 163, the infusion pump is turned on, the aspiration pump is turned off, the aspiration timer is cleared, an infusion timer is started and the pressure compared to the upper operating pressure limit 168. If the pressure is less than the upper operating pressure the elapsed time of infusion is compared to the maximum infusion time parameter 176. If the elapsed time is greater than the allowed time 176, indicating a leakage of solvent out of the gallbladder, the alarm subroutine is called in an alarm (0) condition 178.

If the pressure is greater than the upper operating pressure limit, the infusion pump is turned off, the aspiration pump is turned on, the infusion timer is cleared, and the aspiration timer is again started. The pressure is again compared to the lower operating limit 184 and if it is less than the lower operating limit, the aspiration timer is cleared, the infusion pump is turned on and the aspiration pump is turned off 187.

If the pressure exceeds the lower operating pressure limit 184, the aspiration timer is compared to the maximum aspiration time parameter 186 and if the elapsed time exceeds the maximum time allowed, indicating that aspiration is unable to reduce the pressure, the alarm subroutine is called in the alarm (0) condition. If the elapsed time is less than the maximum aspiration time, the pressure comparison cycle is repeated 184.

Once the infusion pump is on and the aspiration pump is off 187, the pressure is compared to the operating set pressure 189 and if it is less, the pressure comparison loop is repeated. If the pressure exceeds the operating point the subroutine simply returns to the main routine.

Figure 12B:
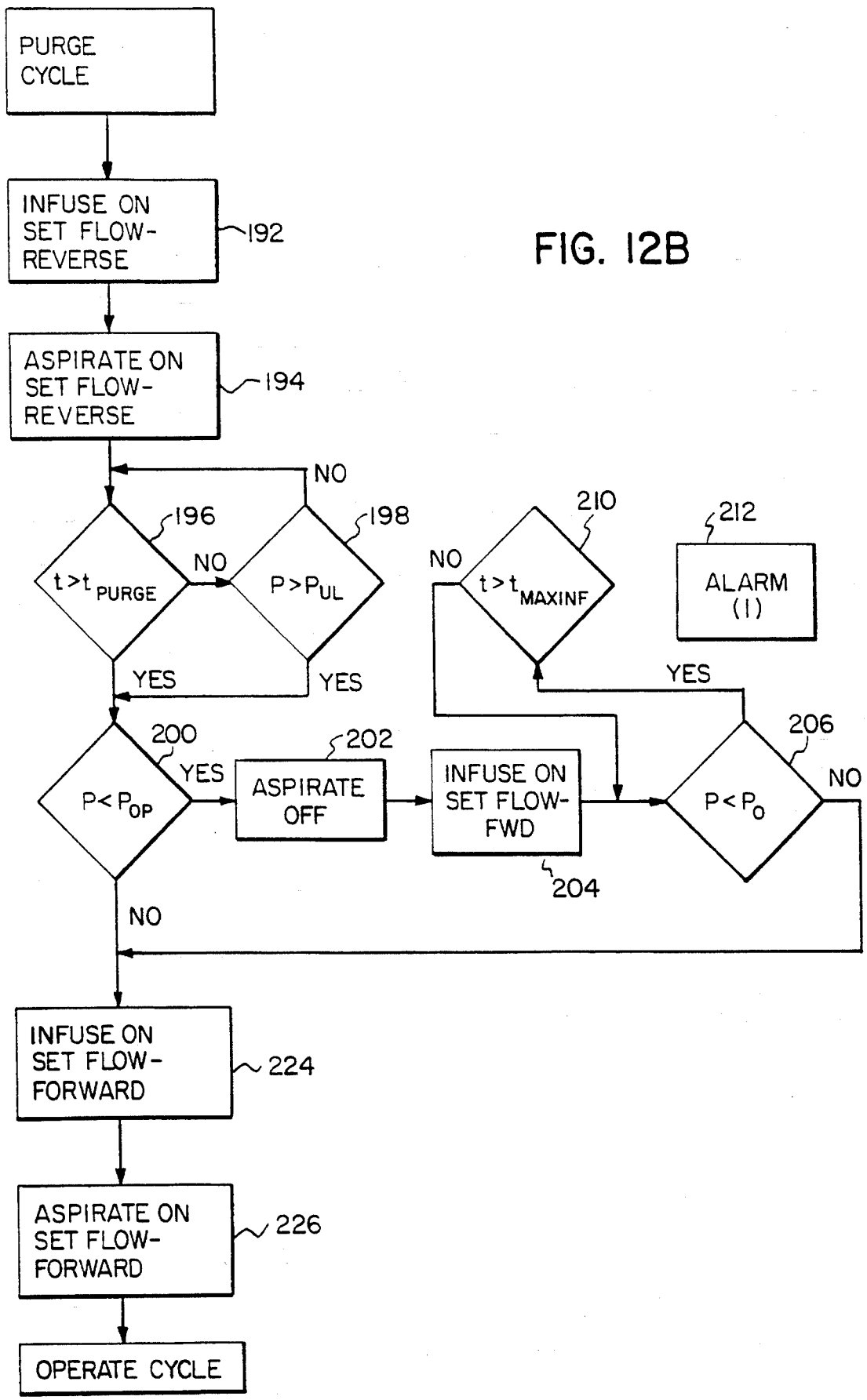
FIG. 12B is a flow diagram of the purge subroutine of FIG. 12.
Figure 12C:
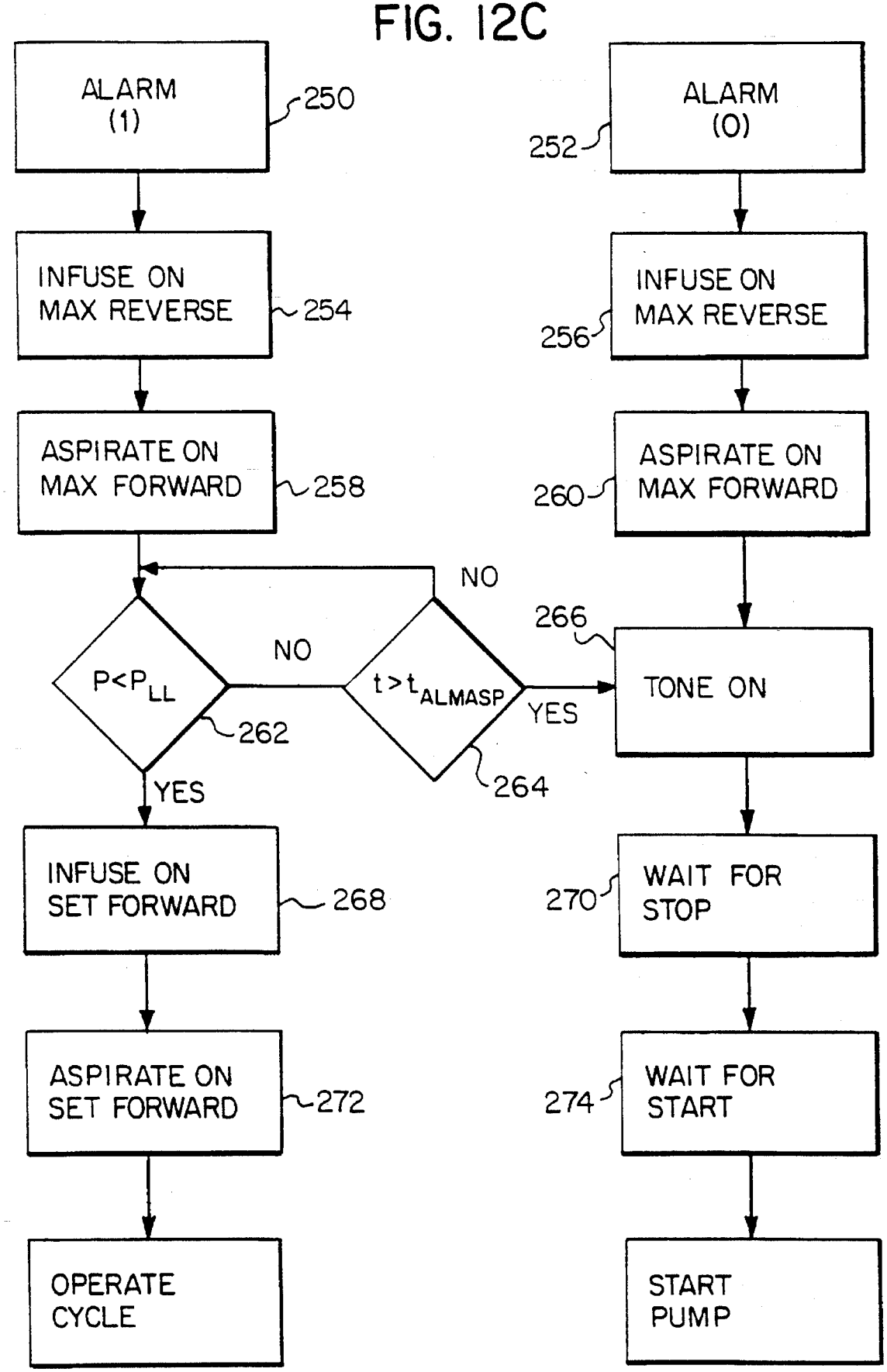
FIG. 12C is a flow diagram of the alarm subroutine of FIG. 12.
Figure 12D:
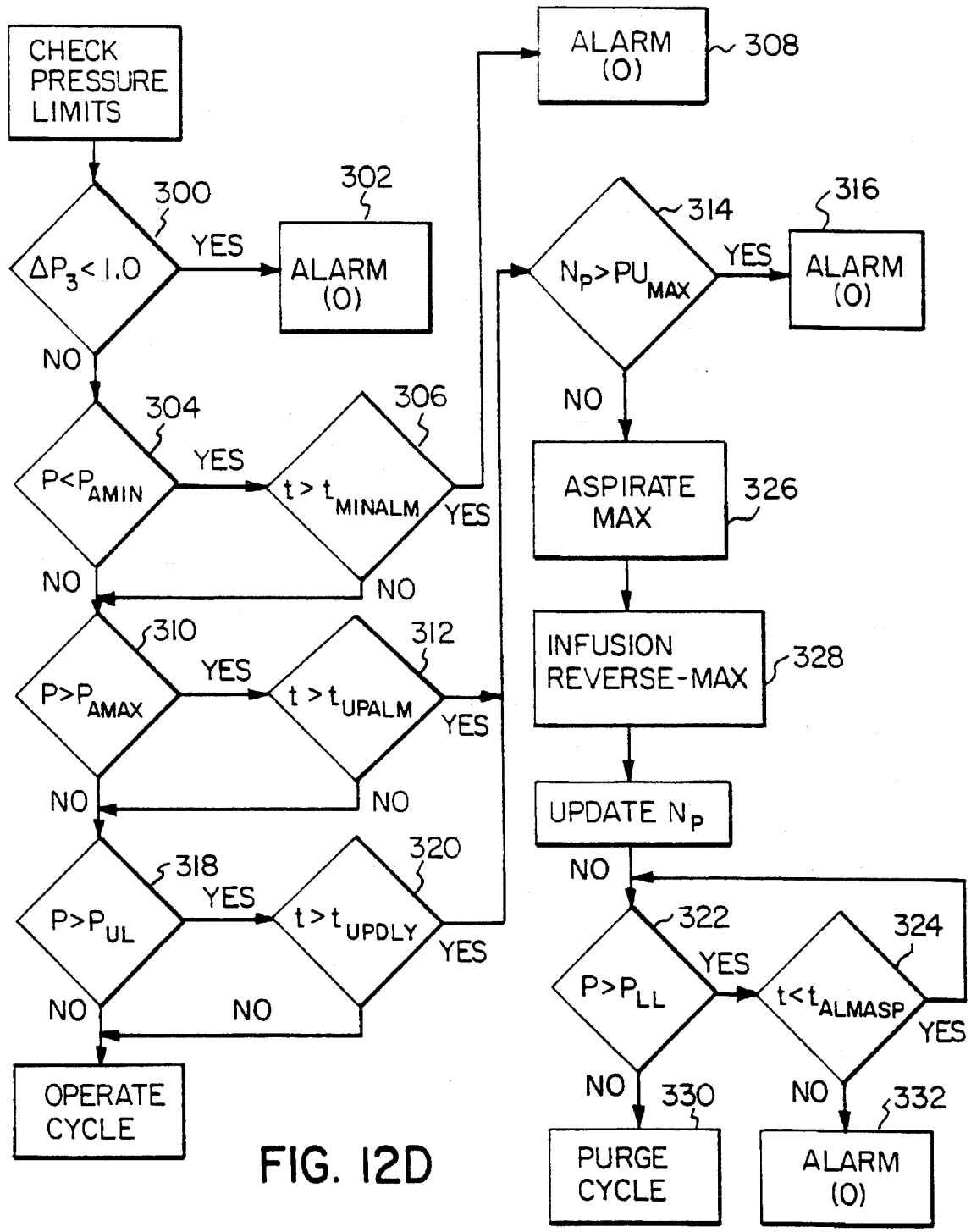
FIG. 12D is a flow diagram of the check pressure limits subroutine of FIG. 12.
Figure 12E:
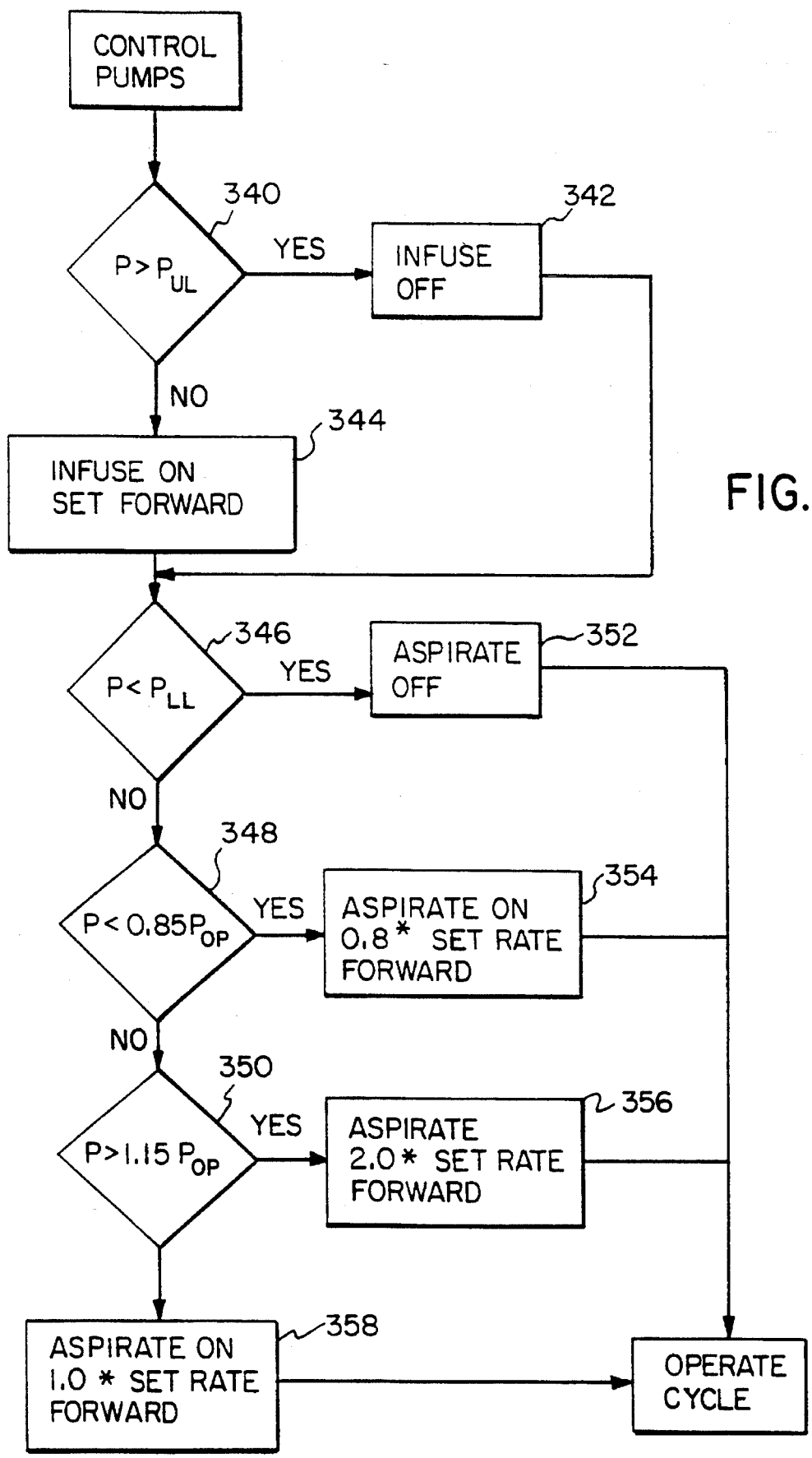
FIG. 12E is a flow diagram of the control pumps subroutine of FIG. 12.

When the it is determined that the aspiration pump is unable to aspirate sufficiently to maintain pressure within the requisite range below the upper pressure limit, the CHECK PRESSURE subroutine causes both pumps to maximally aspirate, and if the lower pressure limit can be attained and the allowed number of purges have not been exceeded 314, 326, 328, 322 and 330 of FIG. 12D, it is assumed that the aspiration port is blocked and that a purge should be attempted. The PURGE subroutine is called to reverse flow through the aspiration and infusion lumens in an attempt to clear the aspiration lumen. Referring to FIG. 12B, the PURGE subroutine first starts a purge timer 196, and sets both the infusion and aspiration pumps in reverse 192, 194 at the set flow rates in an attempt to clear the aspiration lumen. The elapsed time from the purge timer is compared 196 to the purge cycle period, and the purge cycle is allowed to continue if the elapsed time indicated by the purge timer is less than the purge cycle period and the pressure of the fluid in the gallbladder is less than the upper operating pressure limit parameter 198. If the pressure is less than the upper operating pressure limit, the purge continues and the elapsed time compared 196 again. If the pressure exceeds the upper pressure limit 198, the program will proceed through decision point 200, and the pressure check subroutine which will cause maximum aspiration and another purge cycle again if the number of purge cycles has not been exceeded.

If the purge cycle time is exceeded without exceeding the upper pressure limit, the pressure is compared to the operating set point 200. If the pressure is below the set point, the aspiration pump is stopped 202, and the infusion pump is operated at set point in the forward direction. If the pressure does not attain the operating set point 206 within the maximum infusion time, the system calls alarm (1). If the operating set point is attained within the time parameter 210, the system returns to the operate cycle through 224 and 226.

If, upon the completion of time 196, the pressure is above the set point, the infusion and aspiration pumps are turned on in the forward direction 224,226 and the program returns to the operate cycle.

There are two alarm conditions depending upon whether an abnormal pressure condition is recoverable (alarm (1) condition) or whether the condition is so hazardous that normal operation should not be resumed (alarm (0) condition). In either case the first priority is to aspirate from both lumen to reduce the pressure. If the lower pressure limit can be attained within the alarm aspiration time, an alarm (1) condition occurs and normal operations are resumed. If the condition is an alarm (0), a warning is given and the operator must intervene to stop aspiration. Referring to FIG. 12C, the ALARM subroutine, is entered in one of two states: alarm (0) 252, and alarm (1) 250. In either state, the infusion pump is set to maximum reverse 254, 256 while the aspiration pump is set to maximum forward 258, 260 to generate maximum aspiration. If the alarm (0) state 252 was entered, a tone is set 266, and aspiration is continued until the pumps are stopped by operator intervention 270. No further pumping occurs until the pumps are manually restarted 274.

If the alarm (1) state 250 was entered, a timer is started and the pressure is compare to the lower operating pressure and if it is less than the lower operating pressure, the pumps are set to operate normally, infusing fluid 268 through the infusion lumen and aspirating fluid 272 from the aspiration lumen. If the pressure is above the lower operating pressure, the elapsed time of maximum aspiration is compared to a parameter which determines the maximum time allowable at maximum aspiration and if that time has not been reached the pressure is compared again 262. If the elapsed time exceeds the maximum time allowed, a tone is set 266, the pumps continue to aspirate at maximum rate until they are stopped 270 by manual intervention. No pumping commences until the pumps are restarted manually 274.

The CHECK-PRESSURE-LIMITS subroutine is called by the main routine to determine the proper response to the current pressure. Referring to FIG. 12D, the CHECK-PRESSURE-LIMITS subroutine begins by starting a timer to measure elapsed time and calculating the pressure change in the last three seconds. If the pressure change is less than 1 torr, it is assumed that the pressure transducer is not operating correctly and the alarm subroutine is called in the alarm (0) state. If the pressure change is greater than 1 torr, the pressure is compared to the minimum alarm pressure 304 and if the pressure is less than the minimum alarm pressure, the elapsed time indicated by the timer is compared to the minimum alarm pressure trigger time parameter 306. If the time is greater than the minimum alarm pressure trigger time, then, the pressure has been below the minimum allowable pressure for too long, and the alarm subroutine is called in the alarm (0) state. If the time is less than the minimum pressure alarm trigger time, the pressure is compared 310 to the maximum alarm pressure and if it is less the maximum alarm pressure is compared to the upper pressure limit 318.

In either case, the elapsed time is compared to the upper pressure alarm trigger time 312, 320 and if the upper pressure alarm trigger time is exceeded, the number of purges is compared to the number allowed 314 and if too many purges have occurred, the alarm subroutine is called in the alarm (0) state 316.

If the number of purges has not been exceeded, the aspirate pump is set to maximum flow 326. The infusion pump is reversed and set to maximum flow 328, and the counter of the number of purges is incremented. The pressure is then compared to the lower pressure limit 322. If the pressure is below the lower limit within the alarm aspiration time 324 a purge cycle is performed 330, if not the alarm state (0) subroutine is called 332.

If the pressure is below the alarm pressure 310 and the upper pressure limit 318, the pressures are within the desired limits and the system returns to the operate cycle.

When the pressure is below the upper limit and above the lower limit, the CONTROL PUMPS subroutine controls the pumps. Referring the FIG. 12E, the infusion pump will operate until the upper limit is attained 340, 342. The aspiration pump is turned off upon the attainment of the lower limit 346, 352. At pressures between the lower limit and 85% of the set point pressure, the aspiration pump operates at 80% of set flow, 348, 354. At pressures between 115% of set pressure and the upper pressure limit, the aspiration pump operates at 200% of set flow, or maximum flow whichever is lower 350, 356. When the pressure is ±15% of the set pressure, both pumps operate at set flow 358, 344.

The apparatus is completely automatic and is operable without any significant operator input beyond the critical pressure and available volume. Moreover, it is readily converted to a completely closed circuit system in those instances where the therapeutic fluid is combustible. This feature is required for particularly combustible solvents.

Any of a number of types of tubing is suitably used with the pumps of the subject apparatus. However, we have found that tubing composed of "Tygon Special Formulation F-404A" (a vinyl material) or "Nalgene" (a polyurethane) is particularly compatible with solvents such as methyl tert-butyl ether. Moreover, tubing with a large internal diameter is favored for use with peristaltic pumps, enabling a high volume per revolution ratio to be obtained, thereby permitting a low revolution per minute rate to be utilized, hence minimizing torque build-up when a switch over to the high pressure mode leads to pump motor reverse.

As discussed above, the subject apparatus can be utilized for removing obstructions in a variety of organs. However, in the instance where it is used to remove gallstones from gallbladders, perfusion rates of about 50 ml/min to 300 ml/min are generally more effective. This is readily accomplished by manually adjusting the pump speed control circuit 46 of FIG. 2. It is important that the flow rate is sufficient to cause turbulent flow within the gallbladder. It has been found that turbulence increases the rate of gallstone dissolution and helps in removing the non-dissolving fragments.

A variety of catheters usable to deliver and aspirate the fluid can be suitably employed. The catheter must be insoluble in the solvent being infused. For example, a polyurethane catheter is suitable for use with MTBE. Three-lumen catheters as shown in FIGS. 3–5 and 7–8 are favored since pressure measurements as well as perfusion and aspiration of the fluid can all be carried out simultaneously. A suitable three-lumen catheter should have an outside diameter not larger than can be readily employed for the surgical insertion of the catheter into the gallbladder, and should have an aspiration lumen 50, a pressure sensing lumen 52 and an infusion lumen 54. The aspiration lumen preferably should be larger in cross-section than the other two lumen. For the purpose of safety, while achieving effective flow in the system, the aspiration cross-sectional area should be at least 1.5, and preferably about 2.5 times the infusion cross-sectional area. In this way, the volume removed by aspiration can be greater than the volume replaced by infusion under emergency conditions, while allowing a substantial flow to be maintained through the infusion lumen.

Figure 4:
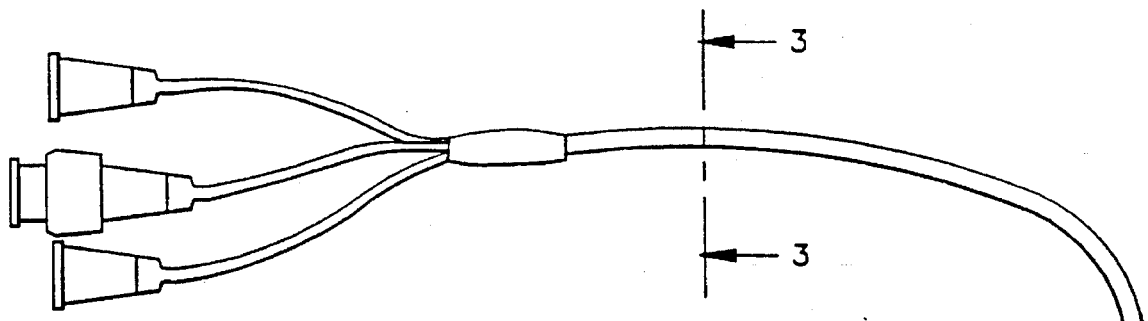
Figure 5:
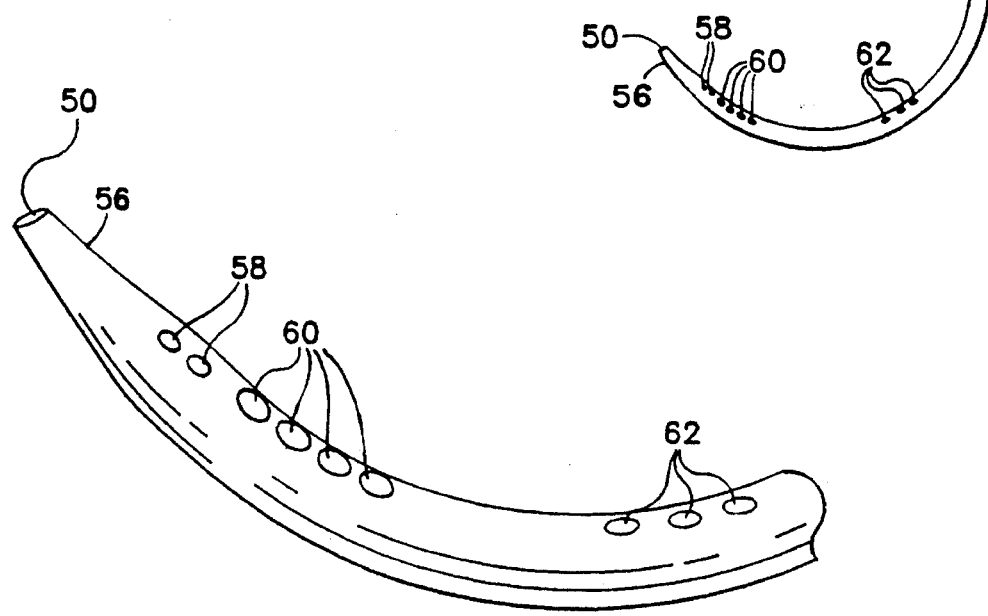

FIGS. 4 and 5 further show another feature of the embodiment of the catheter. It has an elongated tapered tip 56 and holes in the tip 58 and 60 that provide a means for fluid communication with the pressure sending lumen and the infusion lumen, respectively. In addition there are openings 62 in the wall of the catheter that provide a means for communication of fluid between the gallbladder and the aspiration lumen.

Each lumen communicates with the gallbladder through a number of openings in the outside wall of the lumen. The sum of the cross-sectional areas of openings to a lumen should be greater than the cross-sectional area of that lumen in order to minimize flow impedance. The cross-sectional area of each opening should be less than the cross-sectional area of its lumen to prevent debris from obstructing the lumen. The aspiration and infusion openings are distributed along the length of the distal end of the catheter. At least one aspiration opening is located proximal to all infusion openings, preferably being located at the entry point of the catheter into the gallbladder when the catheter is in position for operation. With this configuration, aspiration takes place nearest the insertion point of the catheter into the gallbladder. Any leakage of solvent from the gallbladder through the entry point of the catheter is therefore immediately aspirated and does not damage surrounding tissues.

Figure 11:
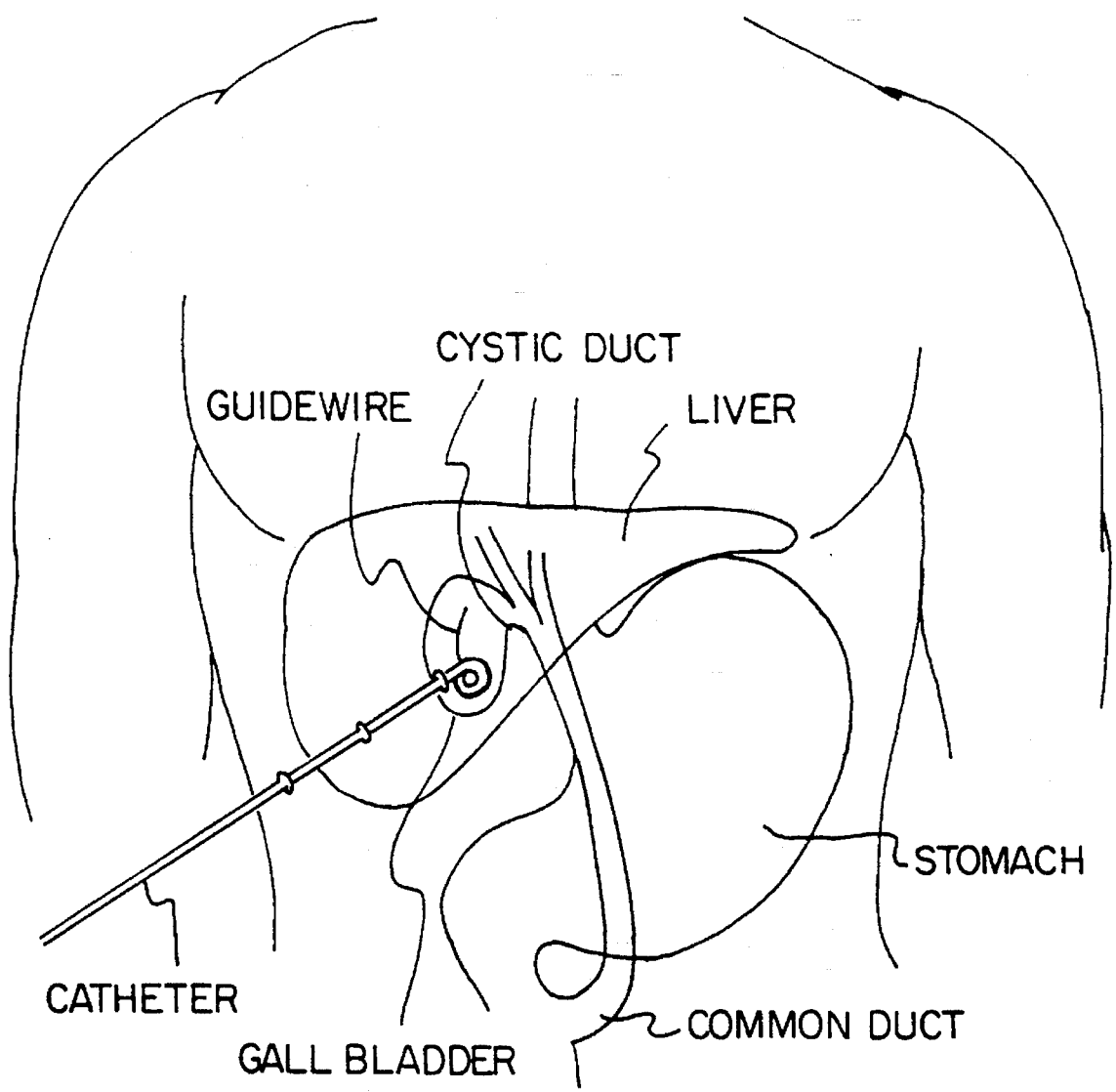
FIG. 11 is a schematic diagram of the catheter of the invention positioned within the gall bladder of a patient.

The aspiration lumen extends to the distal end of the catheter and terminates in an opening at the distal end. Referring to FIG. 11, this opening in the distal end of the catheter also serves as a passageway through which a guidewire can pass. Note that the number of openings is not invariant, depending on the number of gallstones present in the gallbladder, as well as the desirable therapeutic need to effect rapid treatment.

Figure 7:
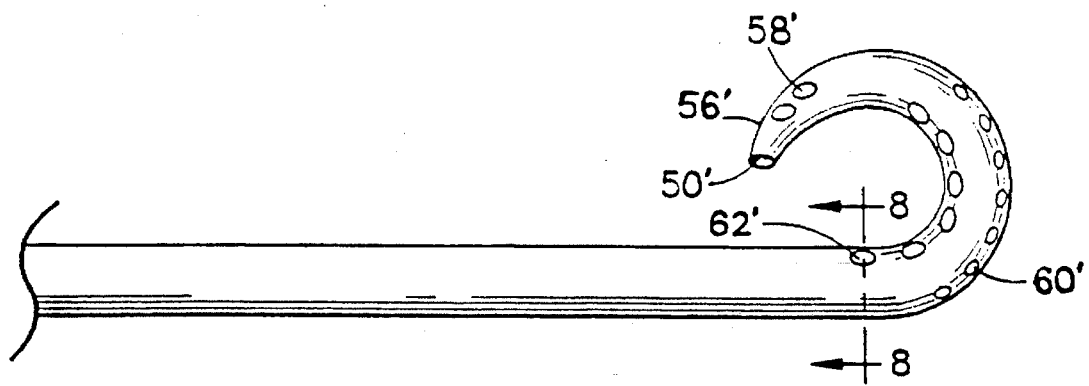
FIGS. 7 and 8 show features of another suitable three-lumen catheter, with FIG. 8 being a sectional view taken on line 8—8 of FIG. 7.
Figure 8:
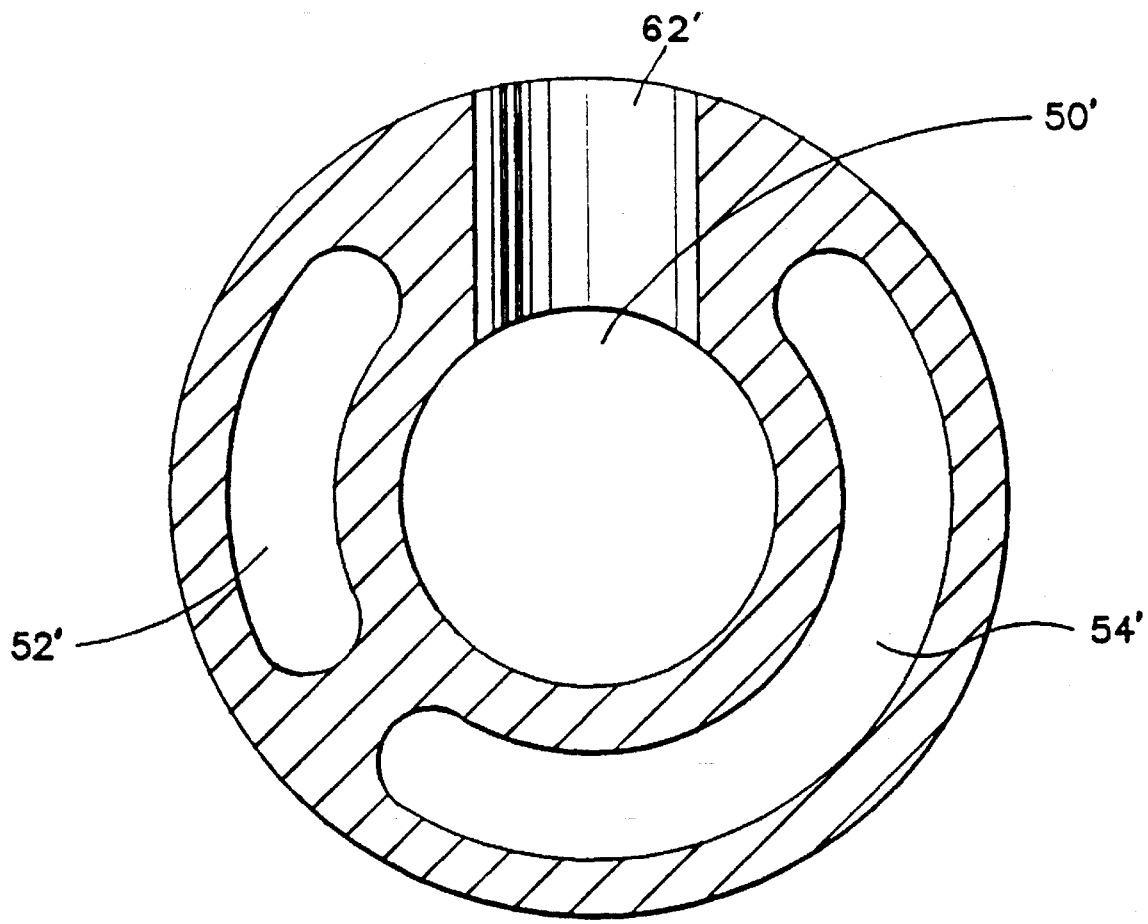
Figure 9:
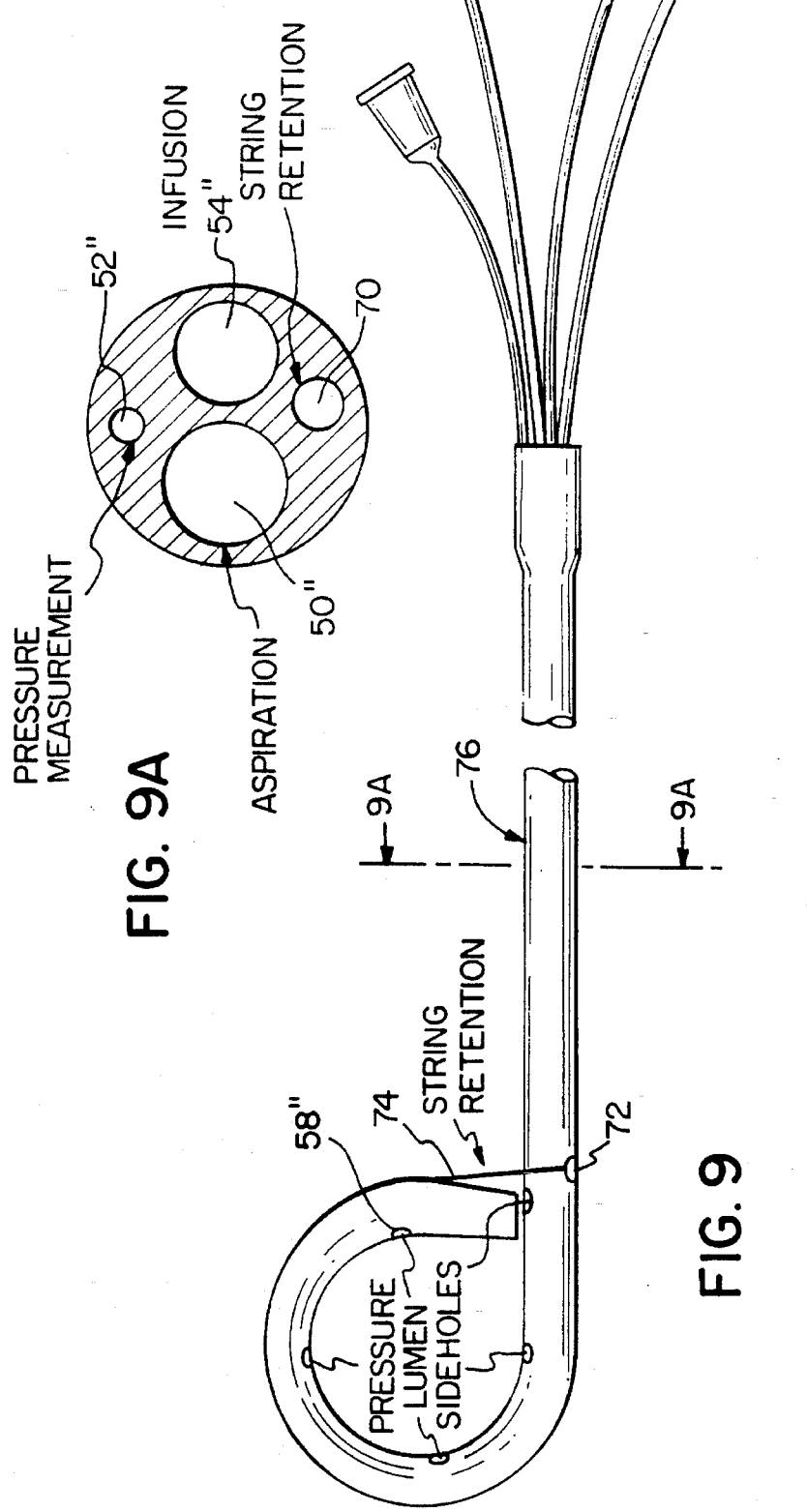
FIG. 9 is a schematic diagram of an embodiment of the catheter portion of the invention in the form of a pigtail catheter.

The distal end of the catheter is preferably curved into a pigtail shape as shown in FIG. 7 to aid in its being retained and positioned in the organ. Referring to FIGS. 9 and 9A, such a pig-tailed catheter can also include a string 74 which helps the catheter retain its pig-tailed shape since fluid being pumped through the catheter and patient movement, coughing or sneezing tends to cause the catheter to unwind. A monofilament or wire can be used in place of a string. The retaining string can either pass through an opening 72 to its own lumen 70 or can pass through the aspiration 50" or infusion 54" lumen. Other means to retain the catheter within the gallbladder are possible. For example, a balloon catheter for example may serve to retain the catheter.

Since the string 74 may pass through its own lumen 52, and since a balloon catheter generally also requires its own lumen, the system should not be construed as being limited to a three-lumen catheter. A variety of catheters of different lumens will perform satisfactorily provided that the system is modified to accommodate such catheters, such modifications being well known to those skilled in the art.

When a pig-tailed catheter is used, openings to the pressure lumen should be located on the inner radius of the curve. This location provides a clear opening for accurate pressure sensing and prevents the mucosa of the gallbladder from interfering with the pressure measurements.

Because this procedure can be inherently dangerous, using toxic and flammable solvents, it is desired that the catheter be used only with the proper pumping system. To assure this, the catheter can have a structural, electrical or fiberoptic connection at its proximal end which is connectable to a similar structure in the remainder of the system. The system may therefore be prevented from functioning with an inappropriate catheter.

It will be appreciated by those skilled in the art that there are numerous modifications in the electrical circuitry, and the overall interconnecting features of the invention that will achieve the efficacious removal of obstructions in particular organs. For instance, while the automatic "self purging" feature of the apparatus is desirable, a device without this feature will perform adequately. Moreover, it should be further noted that, while the invention has been described as applicable to the removal of gallstones from gallbladders, its use should not be so narrowly construed. Thus, it is the intent herein to present an invention that is generally applicable for the removal of obstructions from a variety of organs by dissolving and dislodging the obstruction using solvents.

What is claimed is:

1. A catheter for the contact dissolution of stones in a gallbladder comprising: first and second lumens, each said lumen having distal and proximal portions, said first lumen for infusing solvent and said second lumen for aspirating spent solvent and dissolved gallstones, each of said lumens having at least one opening and all of said openings being in said distal portion for fluid communication between the gallbladder and said lumen, said solvent aspirating lumen having a greater flow crossection than said solvent infusing lumen; and a tension string for holding the distal portion of the catheter in the gallbladder.

2. The catheter of claim 1 wherein the ratio of the cross-sectional area of said aspiration lumen to the cross-sectional area of said infusion lumen is at least 1.5.

3. The catheter of claim 1 wherein the area of each opening is less than the cross-sectional area of the lumen with which said opening is in communication.

4. The catheter of claim 1 further comprising an aspiration opening at the distal end of the catheter in communication with said aspiration lumen.

5. The catheter of claim 1 or 4 having at least one aspiration opening in the wall of the catheter in communication with said aspiration lumen is located proximal to all infusion openings.

6. The catheter of claim 5 wherein said proximally-located aspiration opening is located adjacent to the point of entry of the catheter into the gall bladder when the catheter is in position for operation.

7. The catheter of claim 4 wherein said aspiration lumen and aspiration opening at said distal end of said lumen are constructed and arranged to enable the catheter to pass over a guide wire.

8. The catheter of claim 1 wherein the catheter comprises a material which is resistent to the solvent to be infused into said gallbladder.

9. The catheter of claim 8 wherein the material is polyurethane.

10. The catheter of claim 1 including a third fluid pressure transmitting lumen extending side by side with said infusion and aspiration lumens and having a distal opening in said distal portion of said catheter, said lumen constructed to communicate intra-gallbladder pressure to a remotely located pressure transducer.

11. A catheter according to claim 10 including a fourth lumen and wherein said string is located in the fourth lumen.

12. The catheter of claim 1 including a pressure transducer located in said distal portion of said catheter.

13. The catheter of claim 12 wherein said transducer is piezoelectric.

14. The catheter of claim 12 wherein said transducer is fiberoptic.

15. The catheter of claim 12 wherein the transducer is removably inserted in a lumen of the catheter.

* * * * *